United States Patent [19]
Kolesa et al.

[11] Patent Number: 6,135,996
[45] Date of Patent: *Oct. 24, 2000

[54] CONTROLLED ADVANCEMENT LASING DEVICE

[75] Inventors: Michael S. Kolesa, New Caanan; James Correia, Shelton; Oleg Shikhman, Fairfield, all of Conn.; Thomas J. Pacala, Palm Desert, Calif.; Barton C. Thompson, Redmond, Wash.

[73] Assignee: Baxter International, Inc., Deerfield, Ill.

[ * ] Notice: This patent is subject to a terminal disclaimer.

[21] Appl. No.: 09/062,527

[22] Filed: Apr. 17, 1998
(Under 37 CFR 1.47)

[51] Int. Cl.$^7$ ..................................................... A61B 17/36
[52] U.S. Cl. ................................. 606/15; 606/16; 606/7; 607/93
[58] Field of Search ...................... 606/2, 7, 10, 13–16; 607/88–89, 92, 93

[56] References Cited

U.S. PATENT DOCUMENTS

| | | |
|---|---|---|
| 4,266,548 | 5/1981 | Davi . |
| 4,469,098 | 9/1984 | Davi . |

(List continued on next page.)

FOREIGN PATENT DOCUMENTS

| | | |
|---|---|---|
| 0144764A2 | 6/1985 | European Pat. Off. . |
| 0196519 | 3/1986 | European Pat. Off. . |

(List continued on next page.)

OTHER PUBLICATIONS

Anabtawi IN, Reigler HF, Ellison RG, Experimental Evaluation of Myocardial Tunnelization As A Method of Myocardial Revascularization, Thoracic Cardiovascular Surgery, 58:638–646, 1969.

(List continued on next page.)

*Primary Examiner*—Linda C. M. Dvorak
*Assistant Examiner*—Bryan K. Yarnell
*Attorney, Agent, or Firm*—Baxter Healthcare Corp; Peter Jon Gluck; Bruce M. Canter

[57] ABSTRACT

A controlled advancement laser ablation device is provided for precise ablation of body matter. The laser ablation device includes a handle portion having proximal and distal openings and a fiber advancing device having a stationary member and a movable member. The movable member is movable towards and away from the stationary member. A fiber casing is included having proximal and distal ends. The distal end is secured to the proximal end of the handle portion and the proximal end is secured to the stationary member. At least one optical fiber is included having proximal and distal ends. The distal end is extendible through the handle portion and a portion of the fiber, defined between the proximal and distal ends, is secured to the movable member. A laser energy generator is optically connected to the proximal end of the optical fiber. The handle portion includes a self-biasing advancing mechanism. The self-biasing advancing mechanism includes a guide member positioned within at least a portion of a channel extending within the handle portion. At least one biasing member is operatively connected to the guide member to guide the guide member proximally as a proximal force is applied to the distal end of the optical fiber and to guide the guide member distally when laser energy is transmitted to the optical fiber by the laser energy generator. Controlled advancement mechanisms include constant and/or variable rate springs, motors, and other mechanisms which can be coordinated with the laser energy generator to advance the laser energy transmission mechanism as the targeted substance is ablated. The device is suitable for use in transmyocardial revascularization (TMR) and angioplasty procedures.

7 Claims, 19 Drawing Sheets

U.S. PATENT DOCUMENTS

| | | |
|---|---|---|
| 4,589,404 | 5/1986 | Barath et al. . |
| 4,658,817 | 4/1987 | Hardy . |
| 4,693,244 | 9/1987 | Dalikuzono . |
| 4,760,840 | 8/1988 | Fournier, Jr. et al. . |
| 4,785,815 | 11/1988 | Cohen . |
| 4,830,460 | 5/1989 | Goldenberg . |
| 4,849,859 | 7/1989 | Nagasawa . |
| 4,860,743 | 8/1989 | Abela . |
| 4,913,142 | 4/1990 | Kittrell et al. . |
| 4,928,695 | 5/1990 | Goldman et al. . |
| 4,955,882 | 9/1990 | Hakky . |
| 4,963,142 | 10/1990 | Loertscher . |
| 4,985,028 | 1/1991 | Isner et al. . |
| 4,985,029 | 1/1991 | Noshino . |
| 4,997,431 | 3/1991 | Isner et al. . |
| 5,037,421 | 8/1991 | Boutacoff et al. . |
| 5,096,877 | 3/1992 | Aita et al. . |
| 5,104,393 | 4/1992 | Isner et al. . |
| 5,106,386 | 4/1992 | Isner et al. . |
| 5,109,830 | 5/1992 | Cho . |
| 5,111,832 | 5/1992 | Saksena . |
| 5,112,328 | 5/1992 | Taboada et al. . |
| 5,147,354 | 9/1992 | Boutacoff et al. . |
| 5,163,935 | 11/1992 | Black et al. . |
| 5,188,632 | 2/1993 | Goldenberg . |
| 5,190,536 | 3/1993 | Wood et al. . |
| 5,196,004 | 3/1993 | Sinofsky . |
| 5,222,953 | 6/1993 | Dowltshahi . |
| 5,261,904 | 11/1993 | Baker et al. . |
| 5,288,288 | 2/1994 | Lewis et al. . |
| 5,300,066 | 4/1994 | Manoukian . |
| 5,304,171 | 4/1994 | Gregory et al. . |
| 5,304,172 | 4/1994 | Manoukian et al. . |
| 5,312,396 | 5/1994 | Feld et al. . |
| 5,312,398 | 5/1994 | Hobart et al. . |
| 5,336,215 | 8/1994 | Hsueh et al. . |
| 5,342,352 | 8/1994 | Franken et al. . |
| 5,352,221 | 10/1994 | Fumich . |
| 5,360,426 | 11/1994 | Muller et al. . |
| 5,377,215 | 12/1994 | Das et al. . |
| 5,380,316 | 1/1995 | Aita et al. . |
| 5,389,096 | 2/1995 | Aita et al. . |
| 5,419,312 | 5/1995 | Arenberg et al. . |
| 5,437,660 | 8/1995 | Johnson et al. . |
| 5,441,496 | 8/1995 | Easley et al. . |
| 5,460,182 | 10/1995 | Goodman et al. . |
| 5,464,404 | 11/1995 | Abela et al. . |
| 5,469,524 | 11/1995 | Esch et al. . |
| 5,495,541 | 2/1996 | Murray et al. . |
| 5,496,309 | 3/1996 | Saadat et al. . |
| 5,514,126 | 5/1996 | Prescott . |
| 5,549,601 | 8/1996 | McIntyre et al. . |
| 5,558,668 | 9/1996 | Lankford et al. . |
| 5,558,670 | 9/1996 | Konwitz et al. . |
| 5,575,877 | 11/1996 | Abeta et al. . |
| 5,591,161 | 1/1997 | Negus et al. . |
| 5,603,710 | 2/1997 | Easely et al. . |
| 5,607,420 | 3/1997 | Schuman . |
| 5,607,421 | 3/1997 | Jeevanandam et al. . |
| 5,615,690 | 4/1997 | Giurtino et al. . |
| 5,620,438 | 4/1997 | Ampalz et al. . |
| 5,651,785 | 7/1997 | Abela et al. . |
| 5,672,170 | 9/1997 | Cho et al. . |
| 5,703,985 | 12/1997 | Owyang . |
| 5,713,894 | 2/1998 | Murphy-Chutorian et al. . |
| 5,738,680 | 4/1998 | Mueller et al. . |
| 5,755,714 | 5/1998 | Murphy-Chutorian . |
| 5,766,151 | 6/1998 | Valley et al. . |
| 5,769,843 | 6/1998 | Abela et al. . |
| 5,782,824 | 6/1998 | Abela et al. . |
| 5,782,899 | 7/1998 | Imran . |
| 5,807,383 | 9/1998 | Kolesa et al. ............................. 606/15 |
| 5,807,388 | 9/1998 | Jeevanandam et al. . |
| 5,814,042 | 9/1998 | Zair . |
| 5,873,865 | 2/1999 | Horzewski et al. ...................... 606/15 |

FOREIGN PATENT DOCUMENTS

| | | |
|---|---|---|
| 0325836A2 | 8/1989 | European Pat. Off. . |
| 0481684 | 10/1991 | European Pat. Off. . |
| 0553576 | 1/1992 | European Pat. Off. . |
| 0515867A3 | 12/1992 | European Pat. Off. . |
| 0669107 | 2/1995 | European Pat. Off. . |
| 0737486 | 10/1996 | European Pat. Off. . |
| 0738518 | 10/1996 | European Pat. Off. . |
| 3911796A1 | 10/1990 | Germany . |
| WO80/01238 | 6/1980 | WIPO . |
| WO9314711 | 8/1993 | WIPO . |
| WO9315672 | 8/1993 | WIPO . |
| WO9315676 | 8/1993 | WIPO . |
| WO9315677 | 8/1993 | WIPO . |
| WO9320767 | 10/1993 | WIPO . |
| WO9320768 | 10/1993 | WIPO . |
| WO9401374 | 1/1994 | WIPO . |
| WO9402077 | 2/1994 | WIPO . |
| WO9410922 | 5/1994 | WIPO . |
| WO9410923 | 5/1994 | WIPO . |
| WO9414383 | 7/1994 | WIPO . |
| WO9426184 | 11/1994 | WIPO . |
| WO9505212 | 2/1995 | WIPO . |
| WO9635469 | 11/1996 | WIPO . |
| WO9639962 | 12/1996 | WIPO . |
| WO9639964 | 12/1996 | WIPO . |
| WO9639965 | 12/1996 | WIPO . |
| WO9707735 | 3/1997 | WIPO . |
| WO9713468 | 4/1997 | WIPO . |
| WO9718768 | 5/1997 | WIPO . |
| WO9725101 | 7/1997 | WIPO . |
| WO98/33557 | 8/1998 | WIPO . |

OTHER PUBLICATIONS

Cooley DA, Frazler, OH, Kadipasaoglu K., Pehlivanoglu S., Shannon RL, Angelini P., Transmyuocardial Laser Revascularization: Anatomic Evidence of Long Term Channel Patency, Texas Heart Inst. Journal 21:220–238, 1994.

Crew JR, Transmyuocardial Revascularization by $CO^2$ Laser, Surg, Tech. Intl., 1:236–238, 1991.

Eliseenko VI, Skobelkin OK, Brekhov EI, Zradovsky SF, Morphological Study of Myocardial Revascularization By Laser, Bulletin Exp. Biol. Med., 12:737–739, 1994.

Frazler OH, Cooley DA, Kadipasaoglu KA, Pehlivanoglu S., Lindenmeir M., Barasch E., Congler JL, Wilansky S., Moore WH, Myocardial Revascularization With Laser: Circulation, vol. 92, No. 9:11–58–65, 1995.

Goda T., Wierzbicki Z., Gston A., Leandri J., Vouron J., Loisance D., Myocardial Revascularization By $CO^2$ Laser, Eur. Surg. Res., 19:113–117, 1987.

Goldman A., Greenstone SM, Preuss FS, Strauss SH, Chang ES., Experimental Methods For Producing A Collateral Circulation To The Heart Directly From The Left Ventricle, J. Thorac Surg. 31:364–374, 1956.

Hardy, RI, Bove, KE, James FW, Kaplan S., Goldman L., A Histological Study of Laser–Induced Transmyocardial Channels, Lasers Surg. Med., 6:563–573, 1987.

Horvath KA, Smith WJ, Laurence RG, Schoen EJ, Appleyard RF, Cohen LH, Recovery And Viability of An Acute Myocardial Infaret After Transmyocardial Laser Revascularization.; JAAC., 25:258–263, 1995.

Khazei AH, Kime WP, Papadopoulos C, Cowley RA, Myocardial Canalization: A New Method of Myocardial Revascularization, Ann, Thor. Surg., 6:163–171, 1968.

Kuzela L., Miller GE, Experimental Evaluation of Direct Transventricular Revascularization, J. Thorac. Cardiovascular Surg., 57:770–773, 1969.

Landreneau, R., Nawarawong W., Laughlin H., Ripperger J., Brown O., McDaniel W., McKown D., Curtis J., Direct $CO^2$ Laser *Revascularization* of the Myocardium, Lasers Surg. Med., 11:35–42, 1991.

Lary BG, Effect of Endocardial Incisions on Myocardial Blood Flow, Arch. Surg. Chicago, 87:424–427, 1963.

Massimo C., Boffi L., Myocardial Revascularization By A New Method of Carrying Blood Directly From the Left Ventricular Cavity Into the Coronary Circulation, Thorac. Surg., 36:257–264, 1957.

Mirhoseini M. Cayton MM, Use of Cardioplegia For Laser Revascularization of Myocardium (abstr.), Laaers Surg. Med., 5:169, 1985.

Mirhoseni M., Cayton MM, Muckerheide M., Laser Revascularization of the Heart, SPIE/Lasers Surg. Med., 357, 1982.

Mirhoseni M., Cayton MM, Shelgikar S., Transmyocardial Laser Revasculairization, JACC Abstracts. 1994.

Mirhoseini M., Shelgikar S., Cayton MM, Transmyocardial Laser Revascularization: A Review, J. Clin. Laser Med. Surg., 11:15–19, 1993.

Mirhoseini, M. Revascularization of the Myocardium with Laser, $2^{nd}$ Henry Ford Hospital Int L Symposium on Cardiac Surgery, Appleton–Century–Crofts, New York pp. 595–597, 1977.

Okada M., Ikuta H., Shimizu H., Horii H., Nakamura K., Alternative Method of Myocardial Revascularization By Laser: Experimental and Clinical Study, Kobe J. Med. Sci., 32:151–161, 1986.

Okada M., Shimizu H., Ikuta H., Nakamura K., A New Method of Myocardial Revascularization By Laser, Thorac Cardiovasc. Surg. 39:1–4, 1991.

Pifarre R., Casuja ML, Lynch RD, Neville WE, Myocardial Revascularization By Transmyocardial Acupuncture: A Physiologic Impossibility, J. Thoracic Cardiovasc. Surg., vol. 58, No. 3:424–431, 1969.

Ping T., Liu XJ, Ming SQ, Ren SJ, Xun CX, Xing LH, Ying N., Long I., Experiment Study of $CO^2$ Laser Produce Myocardial Canal, Chinese J. Cardiol. 1990.

Sen PK, Daulstram J., Kinare SG, Udwadia TE, Parulkar GB, Further Studies In Multiple Transmyocardial Acupuncture As A Method of Myocardial Revascularization, Surgery, vol. 64, No. 5:861–870, 1968.

Sen PK, Udwadia TE, Kinare SG, Parulkar GB, Transmyocardial Acupuncture: A New Approach to Myocardial Revascularization, J. Thoracic Cardiovasc. Surg., vol. 50, No. 2:181–189, 1965.

Sen PK, Studies in Myocardial Revascularization, Indian J. Med. Res., 57:415–433, 1969.

Vineberg A., The Formation of Artificial Thebesian Canals in the Wall of the Left Ventricle, Canad M A J, 69:158, 1953.

Vineberg AM, Baichwal KS, Myers J., Treatment of Acute Myocardial Infarction By Endocardial Resection, Surgery, 57:832, 1965.

Wakabayashi A., Little St. Connolly JE, Myocardial Boring for The Eschemic Heart, Arch, Surg., 95:743, 1967.

Walter P., Hundeshagen H., Borst HG, Treatment of Acute Myocardial Infarction By Transmural Blook Supply Frp, The Ventricular Cavity, Eur. Surg. Res. 3:130–138, 1971.

Wearn LT, Mettier SR, Klum TG, Zschiesche AM, The Nature of Vascular Communications Between Coronary Arteries and the Chambers of the Heart, AM Hear J., 9:163–164, 1933.

White M. Hershey JE, Multiple Transmyocardial Puncture Revascularization in Refractory Ventricular Fibrillation Due to Myocardial Ischemia., Ann. Thorac. Surg., vol. 6, No. 6:557–563, 1968.

Whittaker P., Kloner RA, Przyklenk K., Laser–Mediated Transmural Myocardial Channels DO Not Salvage Acutely Ischemic Myocardium. JACC., vol. 22, No. 1:302–309, 1993.

Whittaker P., Rakusan K., Kloner RA, Transmural Channels Can Protect Eschemic Tissue: Assessment of Long–Term Myocardial Response to Laser–and–Needle–Made Channels, Circulation, vol. 93, No. 1:143–151, 1996.

Whittaker P., Zheng SM, Kloner RA, Chronic Response to Direct Myocardial Revascularization: A Preliminary Study, SPIE, vol. 1878:160–166, 1993.

Whittaker P., Zheng SM, Kloner RA, Beneficial Effects of Transmural Myocardial Channels: Chronic Response to Laser and Needle Treatment: AHA Abstracts, $66^{th}$ Scientific Session, 1–435, 1993.

Yano O., Bioelefeld MR, Jeevanandam V., Treat MR, Marboe CC, Spotnitz HM, Smith CR, Prevention of Acute Regional Ischemia With Endocardial Laser Channels, Ann. Thorac. Surg., 56:46–53, 1993.

Kohmoto T., Fisher PE, Gu A., Zhu SM, Yano OJ, Spotnitz HM, Smith CR, Burkhoff D., Does Blood Flow Through Holmium: YAG Transmyocardial Laser Channels?, Ann. Thorac. Surg., 61:861–868, 1996.

Mirhoseini, et al., "Transventricular Revascularization by Laser", *Lasers in Surgery and Medicine*, 2:187–198 (1982).

Mierhoseini, et al., Clinical Report: "Laser Myocardial Revascularization", *Lasers in Surgery and Medicine*, 6:49–461 (1986).

Hardy, et al., "Regional Myocardial Blood Flow and Cardiac Mechanics in Dog Hearts with $CO^2$ Laser–Induced Intramyocardial Revascularization", Basic Research in Cardiology 85:179–177 (1990).

Mirhoseini, et al., "Direct Myuocardial Revascularization: Preliminary Experience", Lasers in Cardiovascular Medicine and Surgery: Fundamentals and Techniques, (Abela, G., ed.), Kluwer Academic Publishers, 385–395.

Mirhoseini, et al., "Myocardial Revascularization by Laser: A Clinical Report", *Lasers in Surgery and Medicine*, 3:242–245 (1983).

Mirhoseini, et al., "Laser Applications in Thoracic and Cardiovascular Surgery", *Medical Instrumentation*, 17:401–403 (Nov.–Dec. 1982).

Jeevanandam, et al., "Myocardial Revascularization by Laser–Induced Channels", *Surgical Forum XL1*, 255–227 (Oct. 1990).

Mirhoseini, et al., "Clinical and Histological Evaluation of Laser Myocardial Revascularization", *Journal of Clinical Laser Medicine & Surgery*, 73–78 (Jun. 1990).

Mirhoseini, et al., "Lasers in Cardiothoracic Surgery", Lasers in General Surgery (Joffe, Editor), Williams and Wilkins, 216–232 (1999).

Mirhoseini, et al., "New Concepts in Revascularization of the Myocardium", The Annals of Thoracic Surgery, 45:415–420 (Apr. 1988).

Mirhoseini, et al., "Revascularization of the Heart by Laser", Journal of Microsurgery, 2:253–260 (Jun. 1981).

Mirhoseini, M., "Laser Revascularization of the Heart", New Frontiers in Laser Medicine and Surgery, (Atsumi, Editor), Elsevier Science Publishing Co., 296–303 (1982).

Mahmood Mirhoseini, MD, FACS, and Mary M. Cayton, RN, *Revascularization of the Heart by Laser, Journal of Microsurgery,* 2:253–260, 1981.

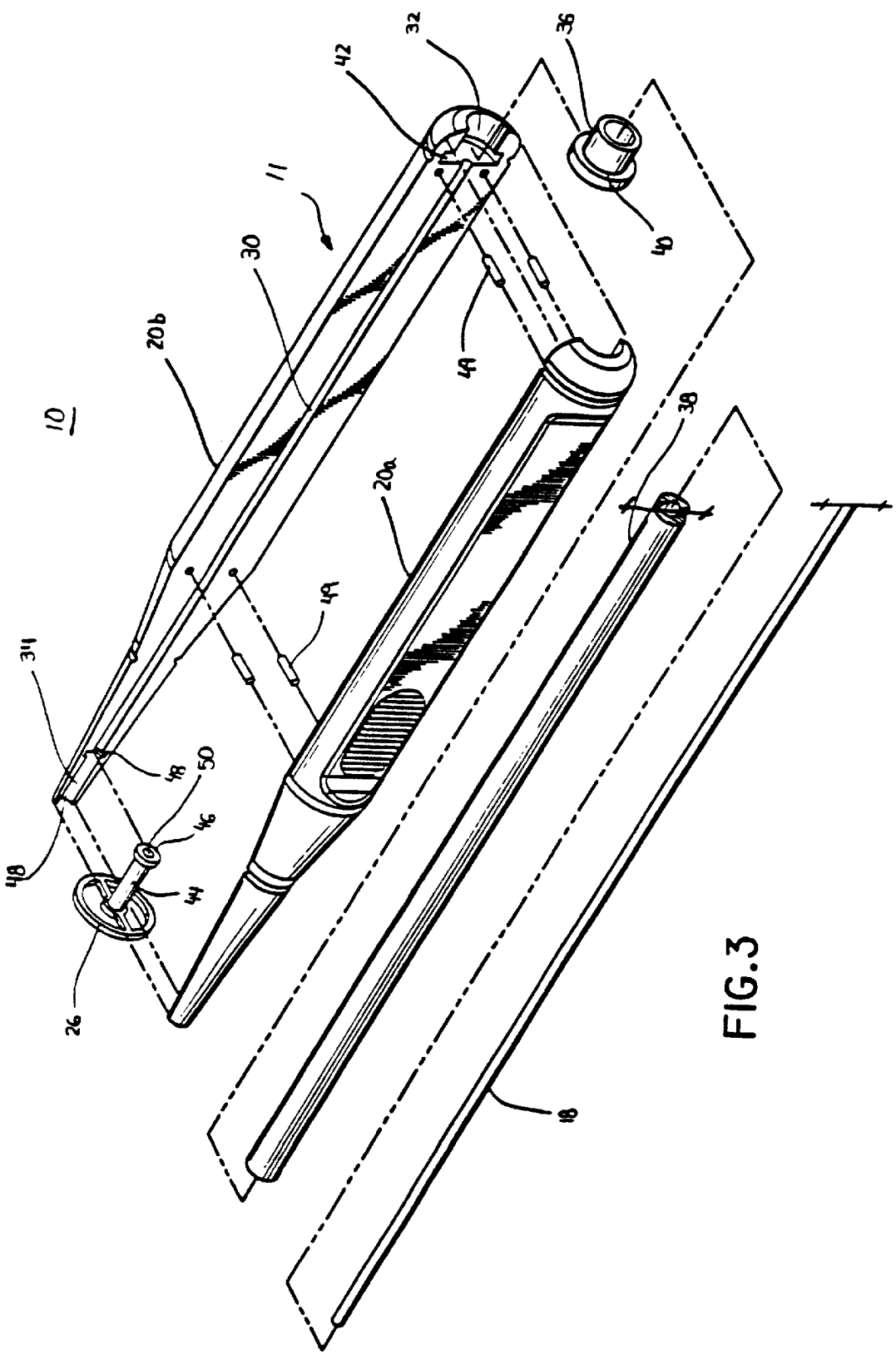

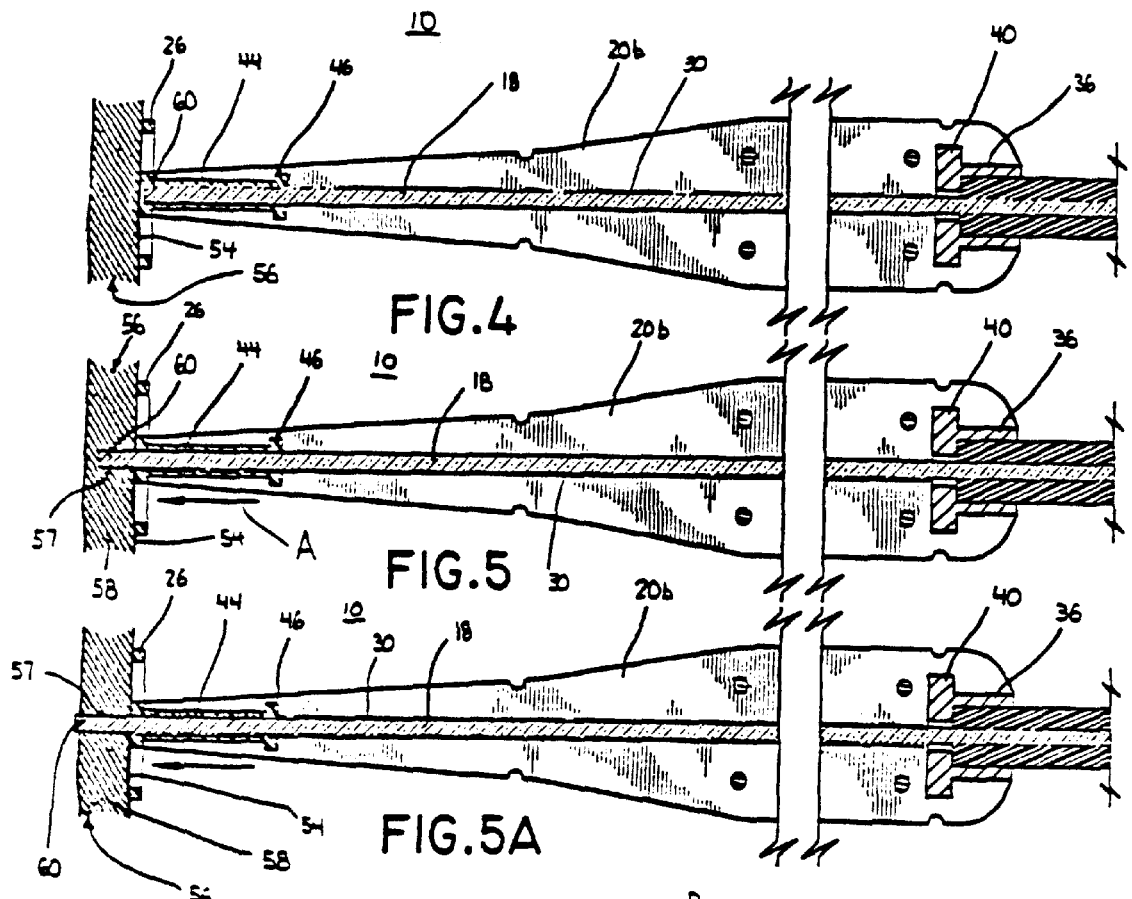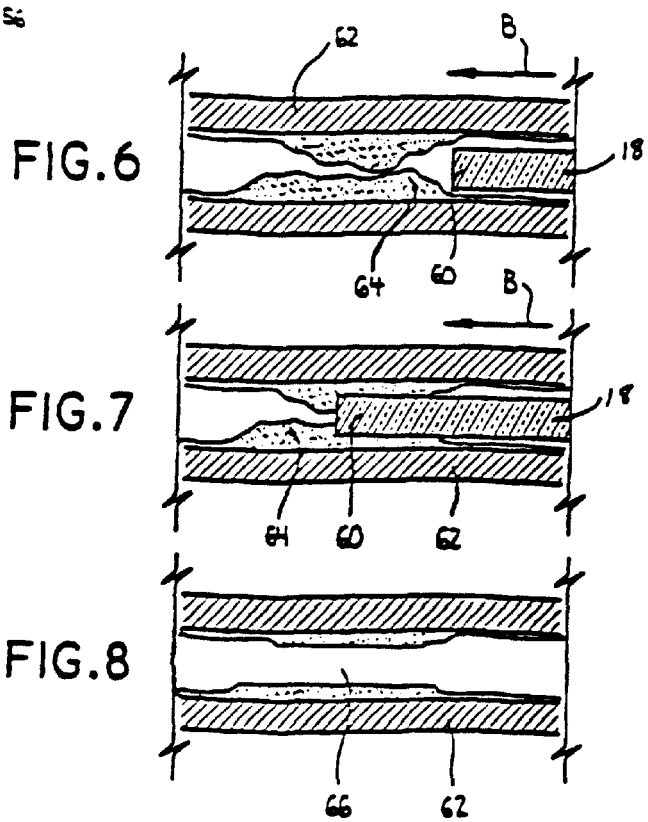

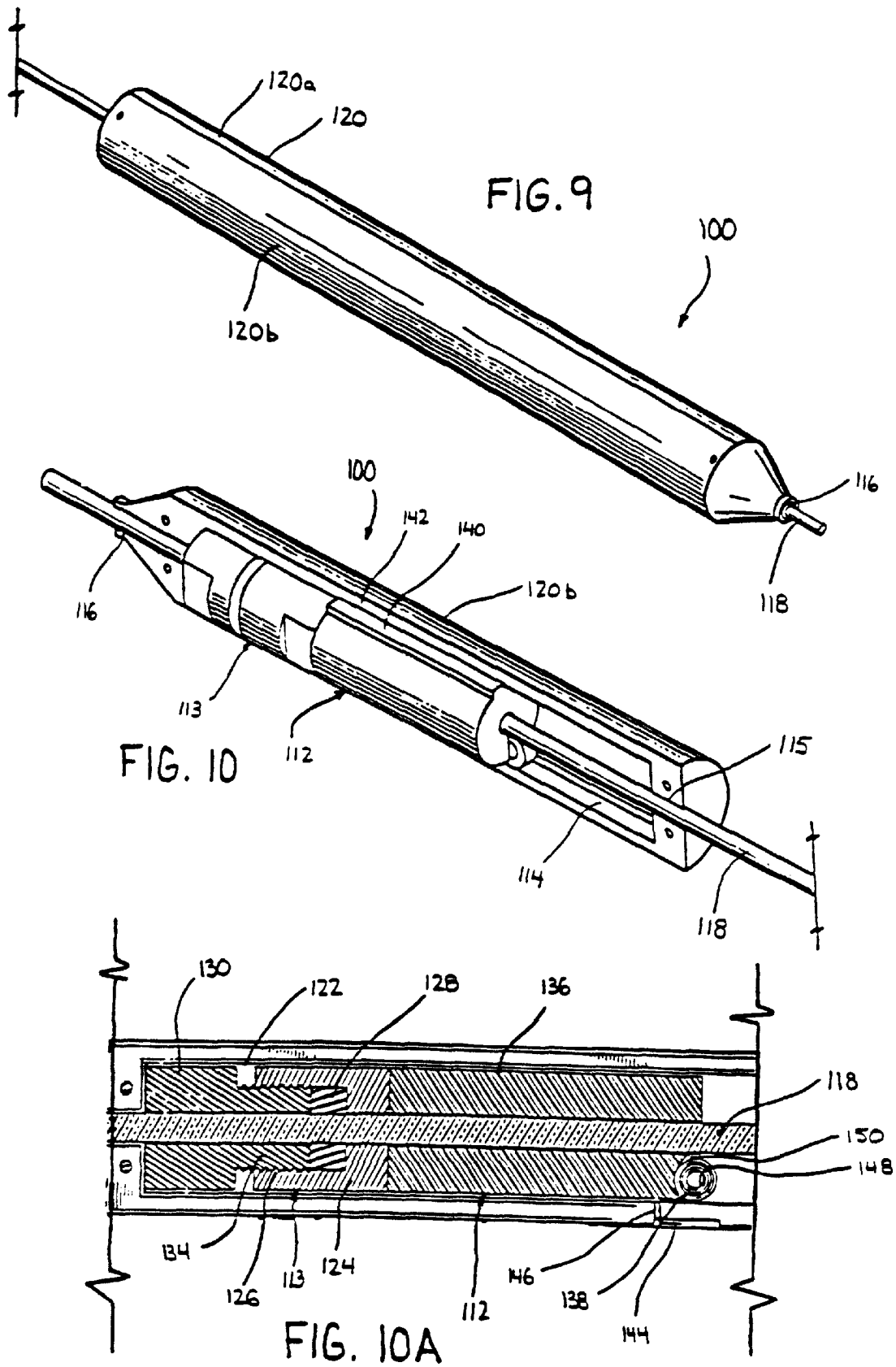

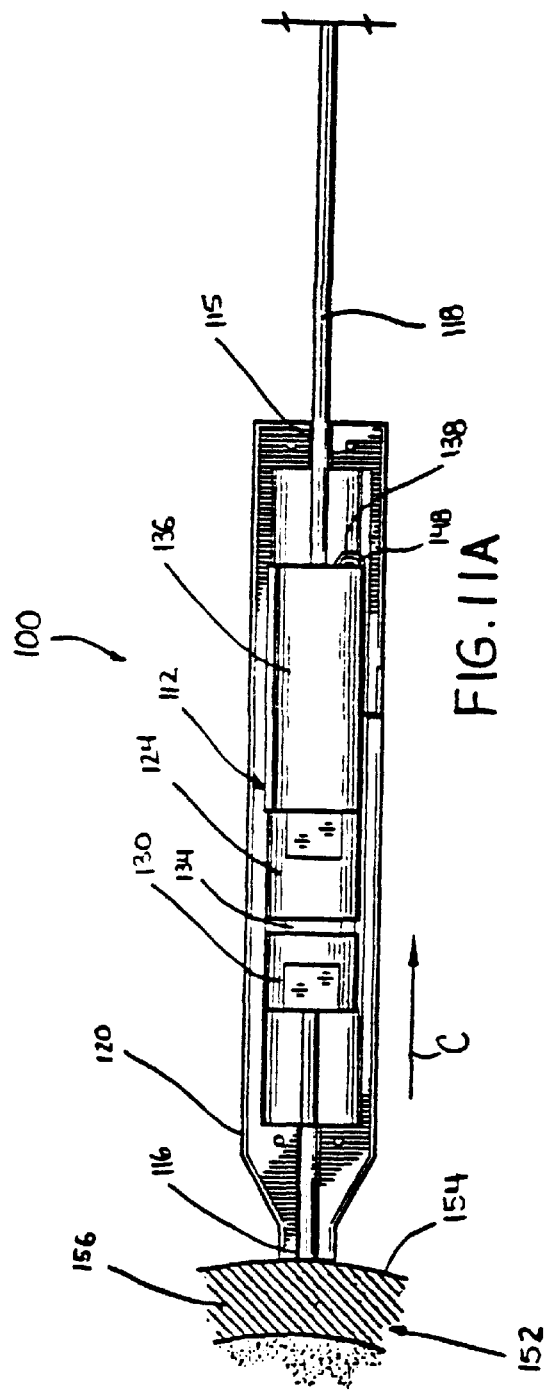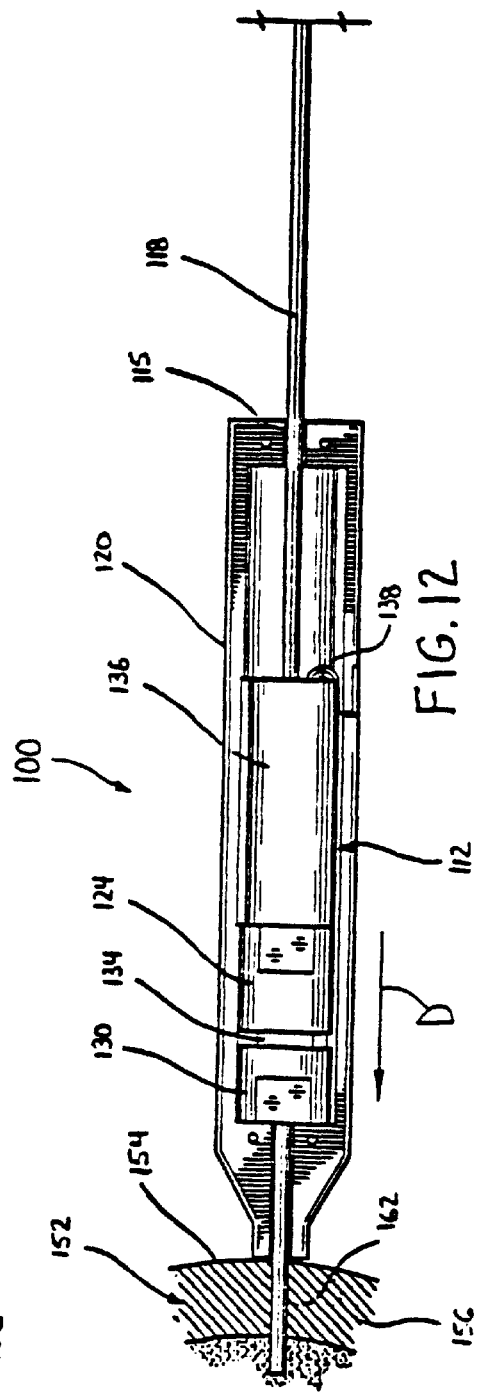

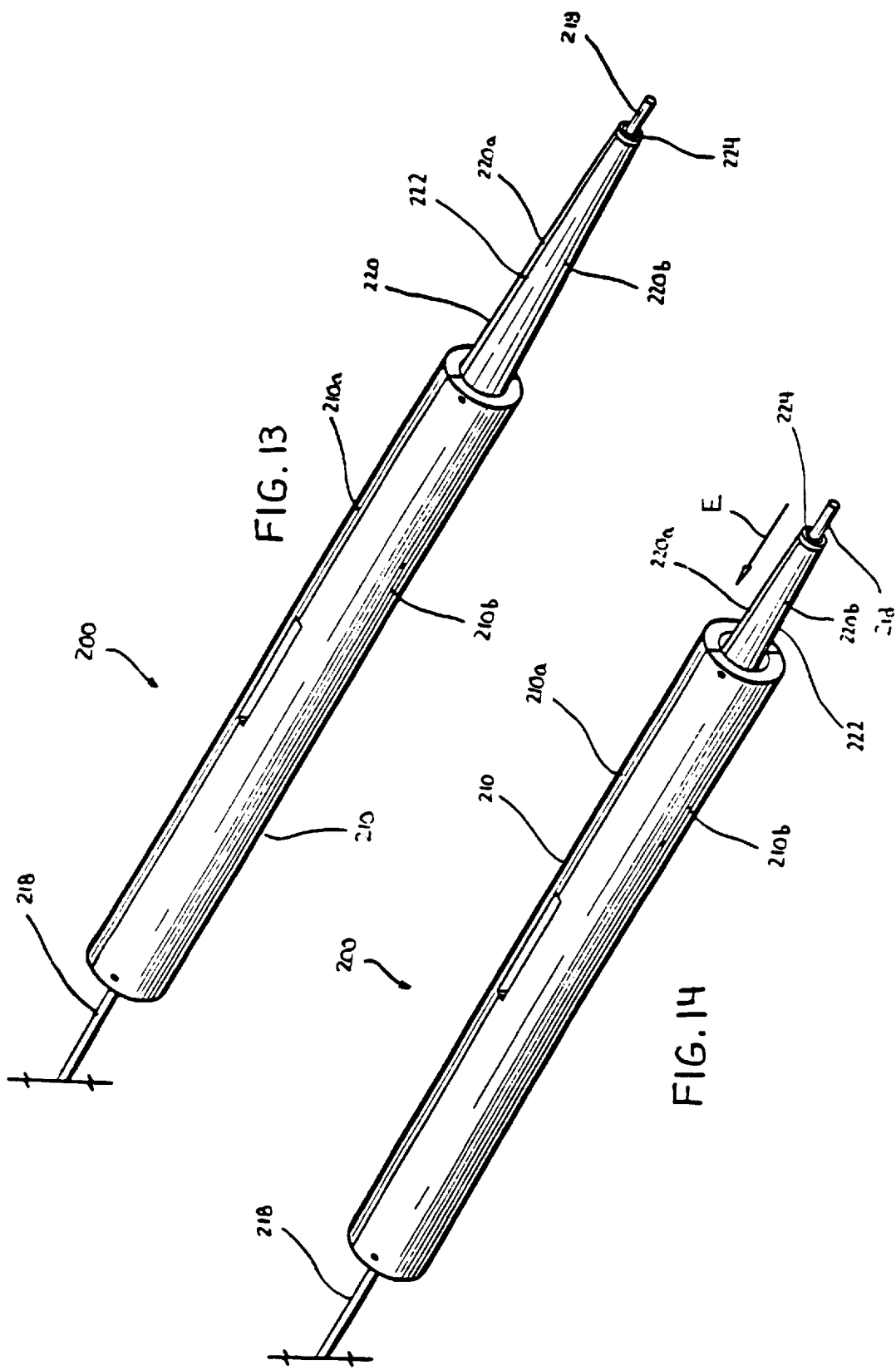

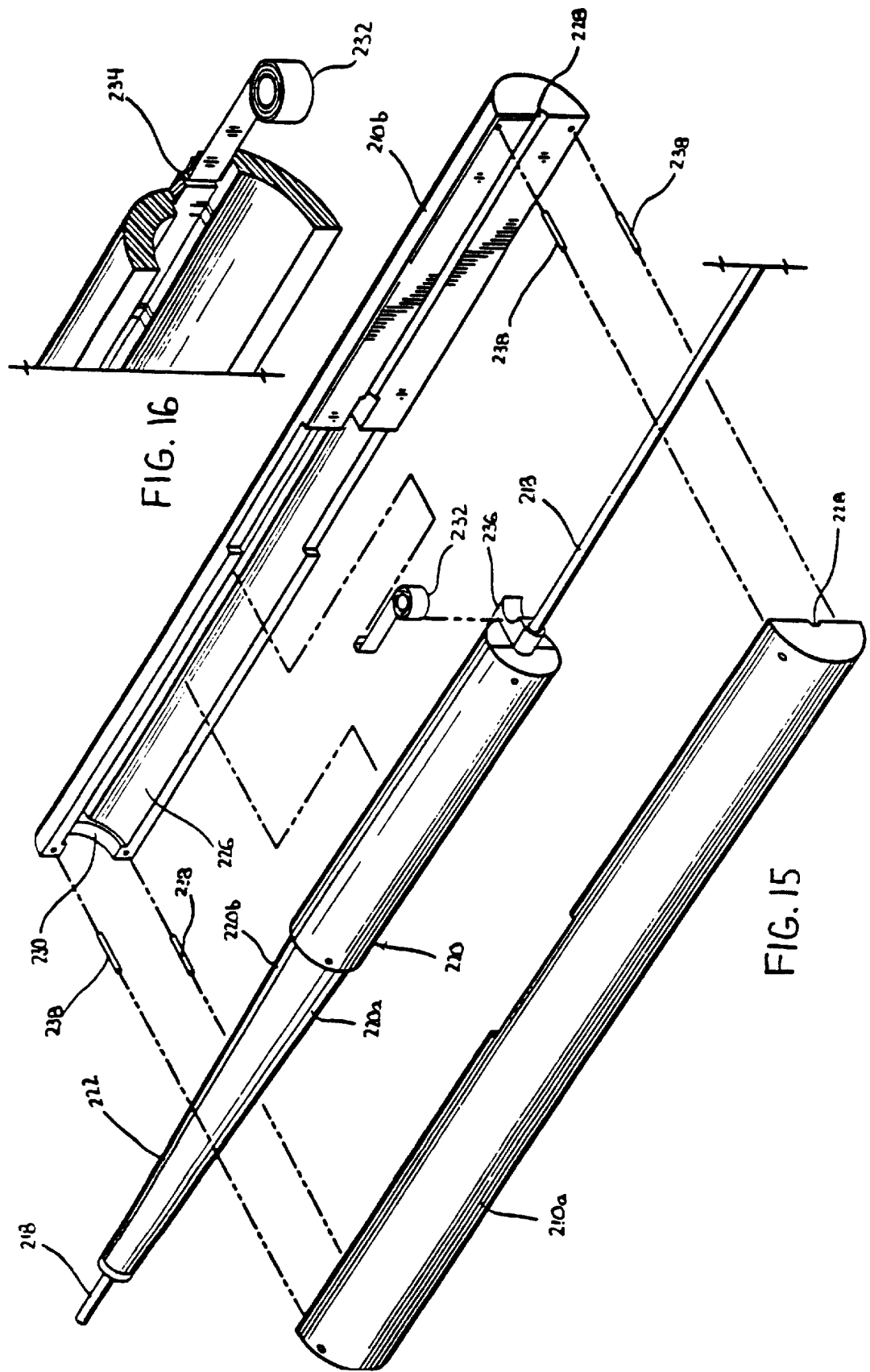

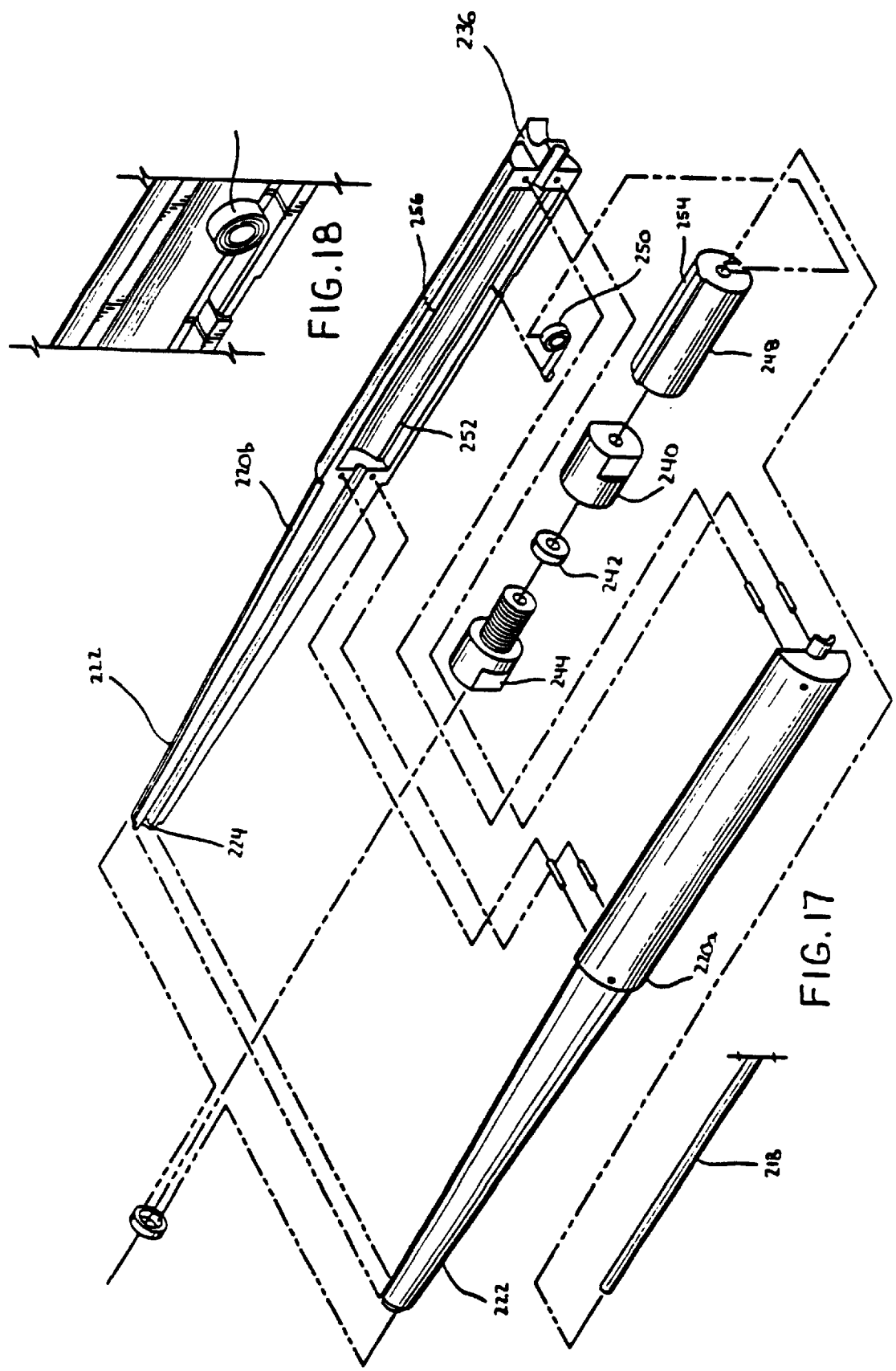

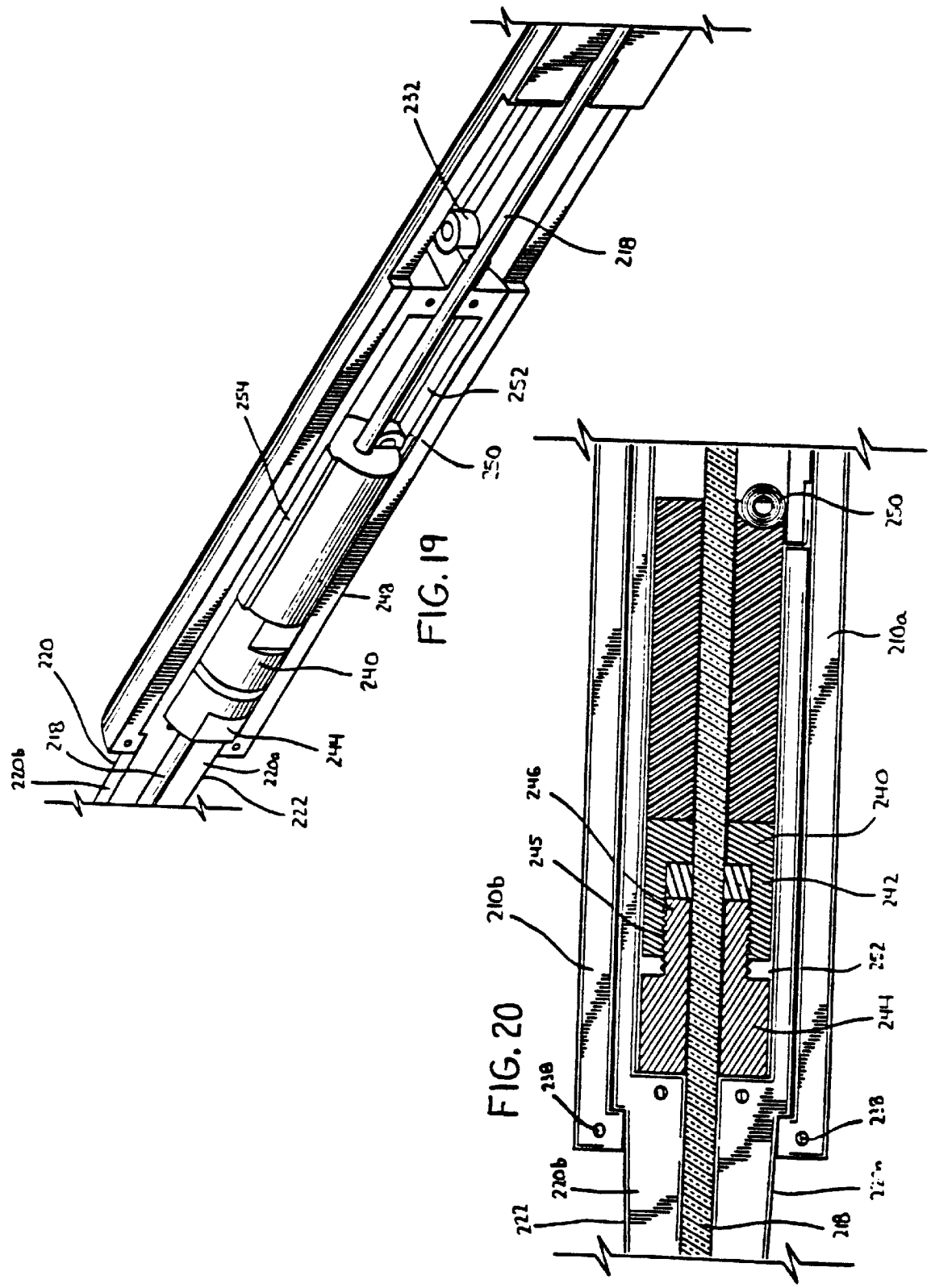

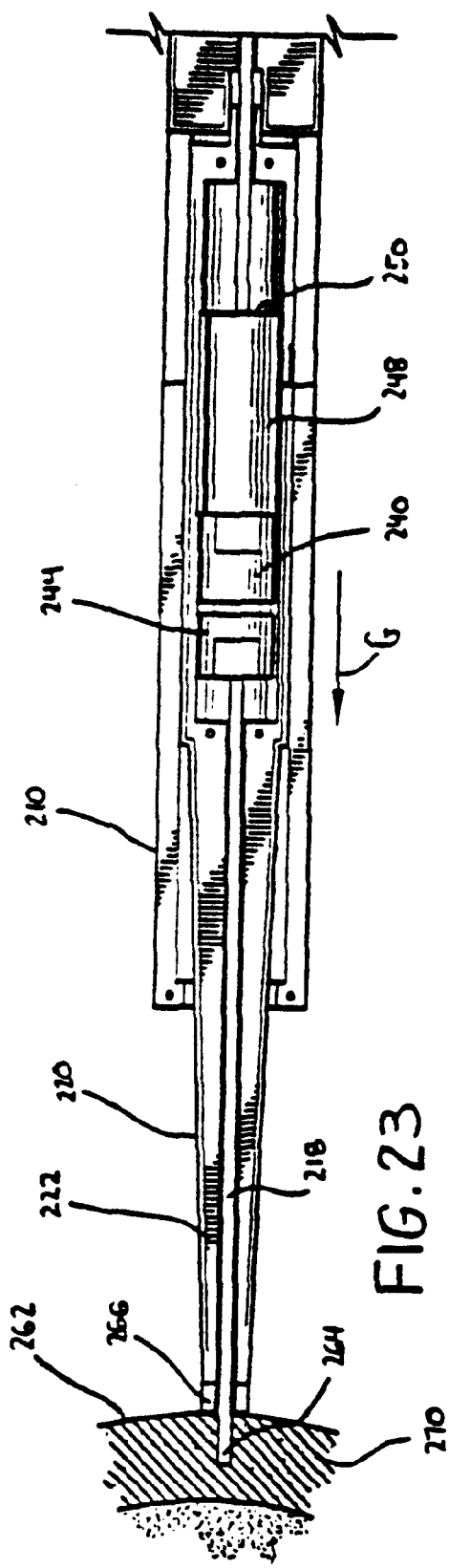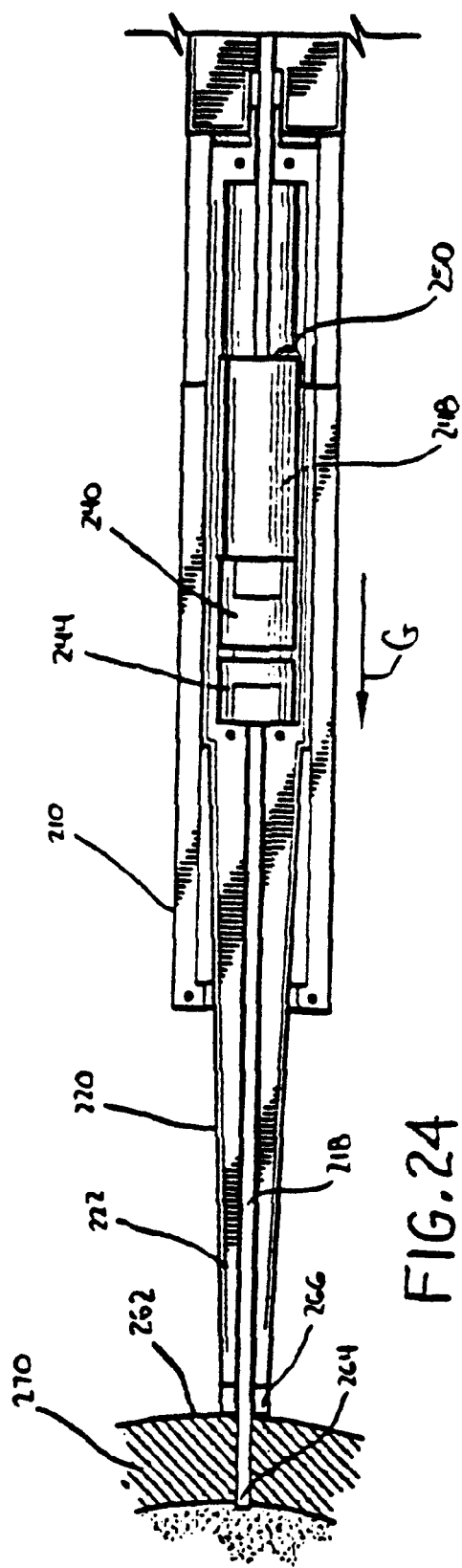

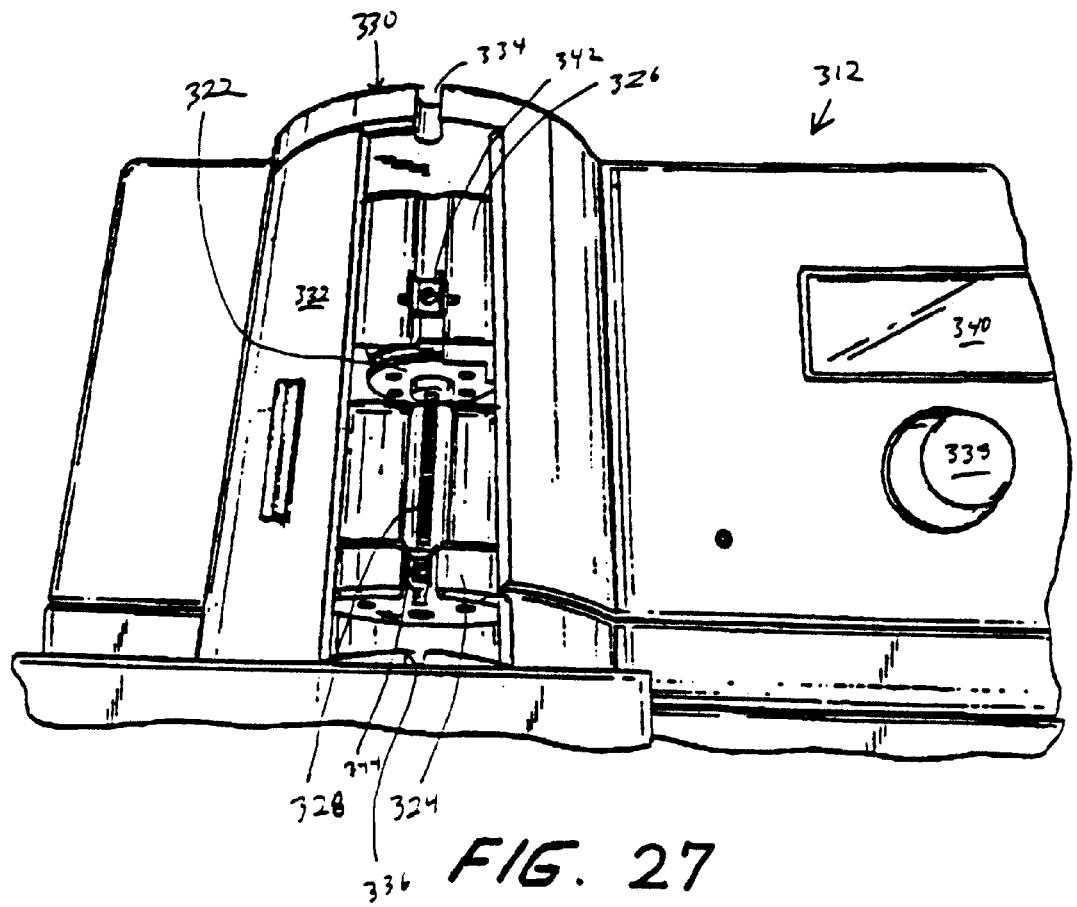
FIG. 27
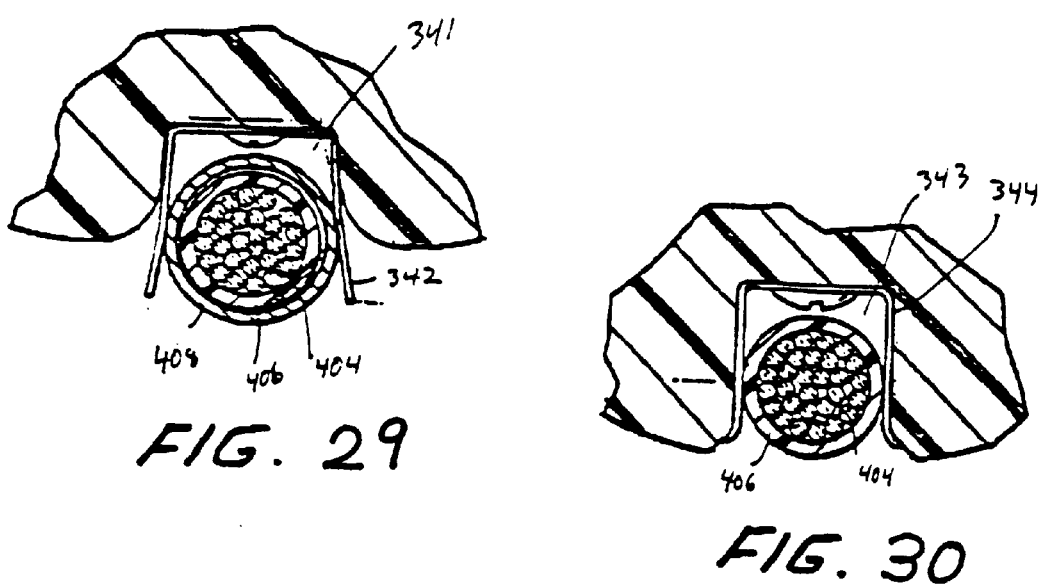
FIG. 29
FIG. 30

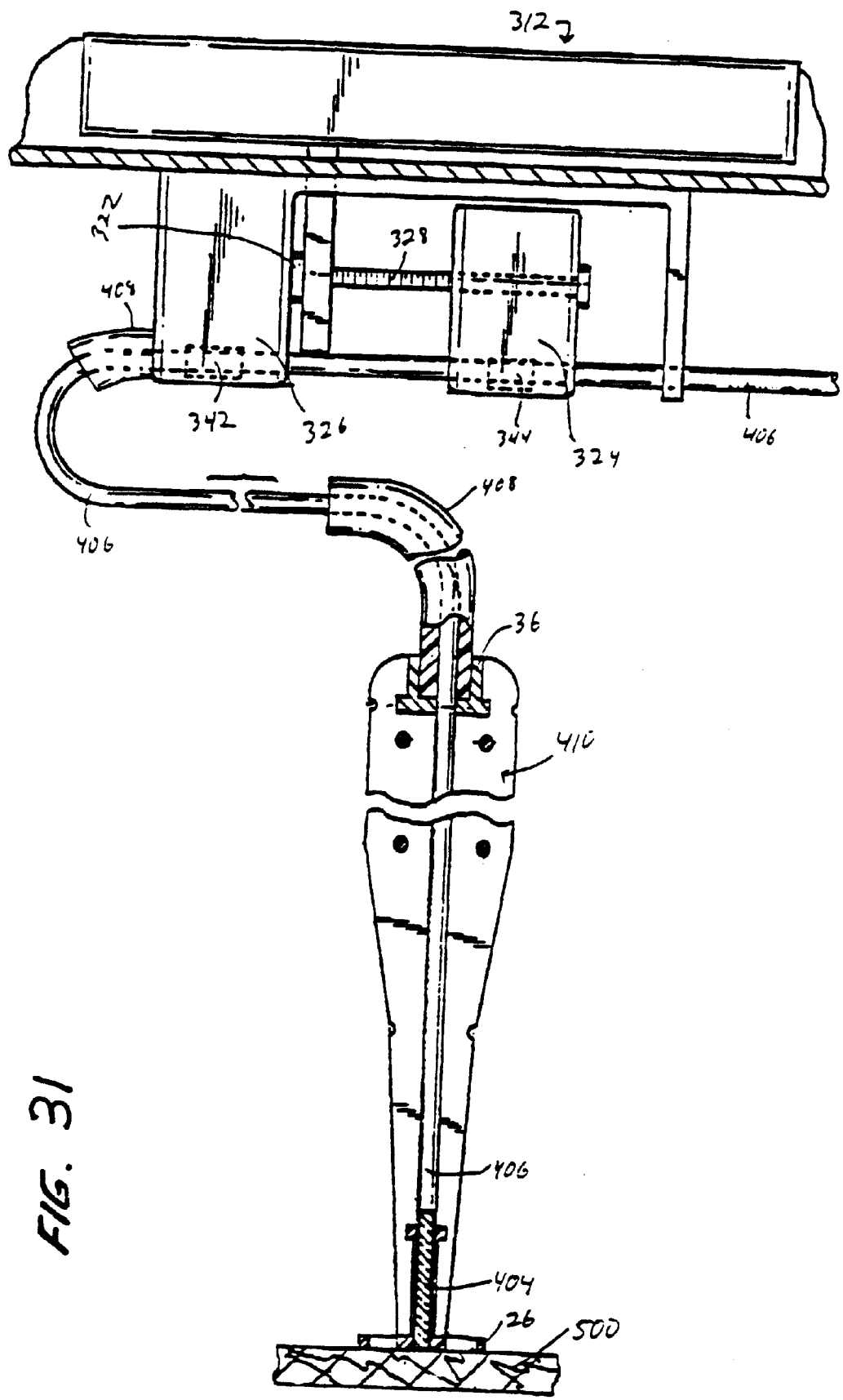

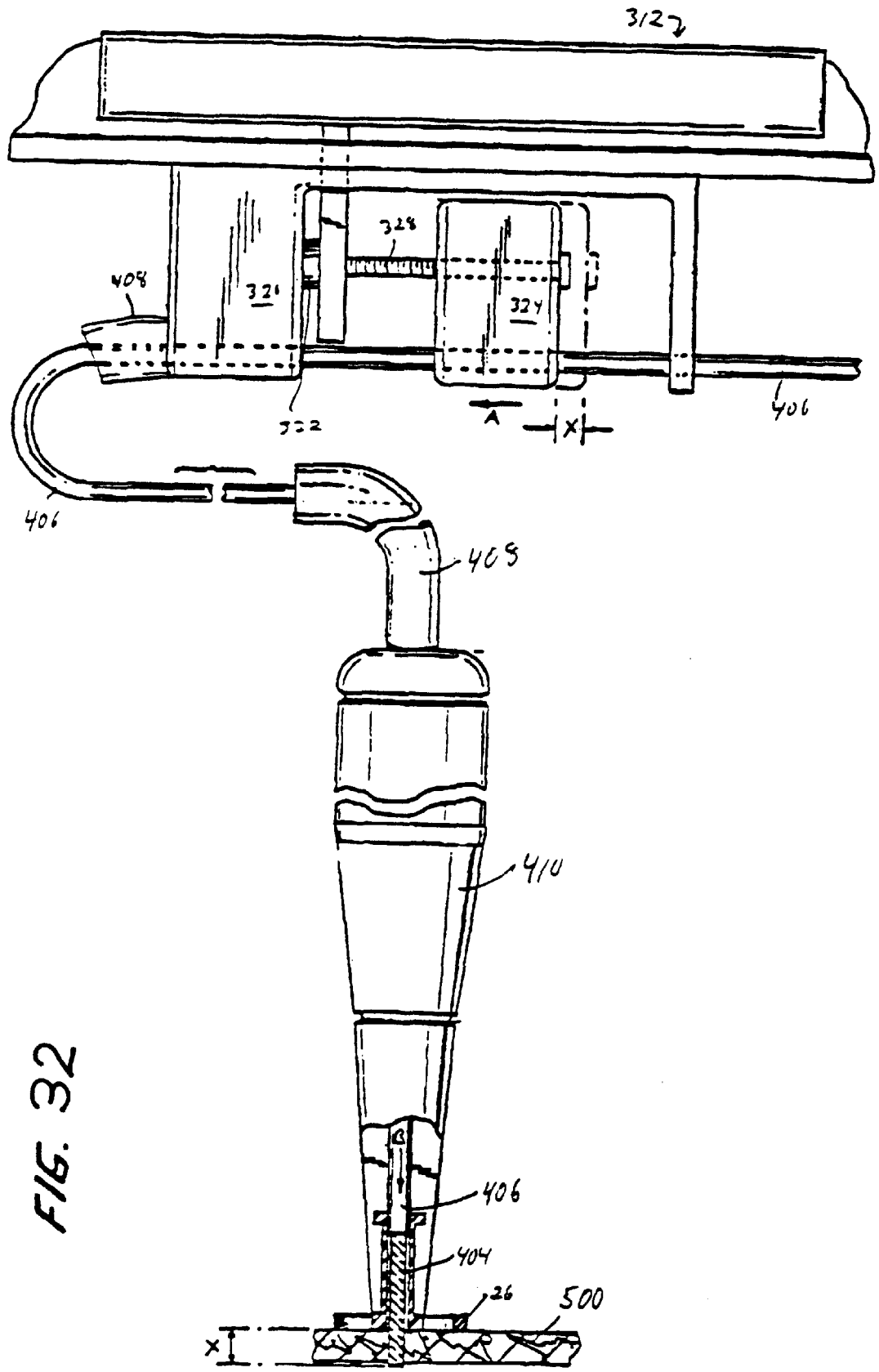

CONTROLLED ADVANCEMENT LASING DEVICE

BACKGROUND

1. Technical Field

The present disclosure relates generally to laser ablation devices for surgical use. More specifically, the present disclosure relates to laser ablation devices having a longitudinally advancing laser energy transmission mechanism to facilitate ablation of body tissue. The laser ablation device is particularly suited for use in performing transmyocardial revascularization (TMR) and angioplasty.

2. Background of the Related Art

A variety of procedures and apparatus have been developed to treat cardiovascular disease. For example, minimally invasive surgical procedures such as balloon angioplasty and atherectomy have received extensive investigation and are in wide use. In some patients, however, circumstances still require conventional open heart bypass surgery to correct or treat advanced cardiovascular disease. In some circumstances patients may be too weak to undergo the extensive trauma of bypass surgery or repetitive bypasses may already have proved unsuccessful.

An alternative procedure to bypass surgery is transmyocardial revascularization (TMR), wherein holes are formed in the heart wall to provide alternative blood flow channels for ischemic heart tissue. This procedure can be done by laser. In early laser myocardial revascularization, a $CO_2$ laser was used to produce holes in the heart wall. In this procedure, laser energy is transmitted from the laser to the heart wall by an externally located articulated support. Thus, some surgical opening of the chest wall is required to access the heart muscle. The entrance wound in the heart is closed by external pressure with the objective that the endocardial and myocardial layers remain open to permit blood flow from the ventricle to the heart muscle.

A less traumatic approach to laser myocardial revascularization is disclosed in U.S. Pat. Nos. 5,380,316 and 5,389,096 to Aita et al. These references disclose methods of myocardial revascularization using a deflectable elongated flexible lasing apparatus which is either introduced through a patient's vasculature or alternatively, directly into the patient's chest cavity. The intravascular method requires the direction of laser energy from inside the heart to form a bore in the heart wall while the other method requires introduction of the lasing apparatus through the patient's chest and into contact with the outer wall of the heart.

In both of these methods, the optical fiber conveying the laser energy is advanced and controlled by hand to form the bore. This manual advancement and control presents problems in that depth and rate of penetration are difficult to accurately reproduce for the multiple bores necessary in a myocardial revascularization procedure.

In addition, if the advancement rate of the laser fiber is too slow, tissue damage from thermal and acoustic shock can result. On the other hand, if the advancement rate of the fiber is too fast (i.e., faster than the laser ablation rate), the fiber itself, not the laser energy, can mechanically form at least a portion of the hole, which may be undesirable.

Similar problems are present in other cardiovascular procedures such as, e.g. laser angioplasty wherein an optical fiber is inserted and manually advanced into a patient's vasculature to apply laser energy to obstructions and/or restrictions typically caused by plaque build-up. Both continuous wave and pulsed high energy lasers have been used to provide the vaporizing laser energy. Insuring the plaque is actually ablated and not just pushed aside is important to prevent or delay restenosis. Once again, because the fiber is manually advanced, the rate of advancement of the fiber through the obstruction is generally uncontrolled.

SUMMARY

In accordance with the present disclosure, a controlled advancement laser ablation device is provided for precise ablation of body matter. The laser ablation device includes a laser energy transmission mechanism such as, e.g. an optical fiber device mounted for controlled longitudinal movement relative to a housing structure. A laser energy generator is optically connected to the laser energy transmission mechanism for initiating laser energy. A controlled advancement mechanism is provided in engagement with the laser energy transmission mechanism for advancing the mechanism through the housing structure at a controlled rate coordinated with the laser energy generator output to ablate body tissue. Controlled advancement mechanisms include constant and/or variable rate springs, motors, and other mechanisms which can be coordinated with the laser energy generator to advance the laser energy transmission mechanism during ablation.

BRIEF DESCRIPTION OF THE DRAWINGS

Various preferred embodiments are described herein with references to the drawings:

FIG. 3 is a perspective view with parts separated of the handle and'fiber optic portion shown in FIG. 2;

FIG. 4 is a side cross-sectional view of the handle portion shown in FIG. 2 engaging body tissue with the optical fiber retracted within the housing of the device;

FIG. 5 is a side cross-sectional view of the handle portion shown in FIG. 2 engaging body tissue with the optical fiber extended into body tissue;

FIG. 5A is a side cross-sectional view of the handle portion shown in FIG. 2 engaging body tissue with the optical fiber extended through the body tissue;

FIG. 6 is a side cross-sectional view of the distal end of the optical fiber of the laser ablation device shown in FIG. 1 extending within vascular tissue;

FIG. 7 is a side cross-sectional view of the distal end of the optical fiber of the laser ablation device shown in FIG. 1 extending into plaque within vascular tissue;

FIG. 8 is a side cross-sectional view of vascular tissue having a channel formed in plaque by the laser ablation device shown in FIG. 1;

FIG. 9 is a perspective view of an alternate embodiment of a handle portion of the laser ablation device;

FIG. 10 is a perspective view of the handle portion shown in FIG. 9 with a half-housing section removed;

FIG. 10A is a side cross-sectional view of the internal components of the handle portion shown in FIG. 10;

FIG. 11A is a side cross-sectional view of the handle portion shown in FIG. 9 engaged with body tissue with the optical fiber retracted;

FIG. 12 is a side cross-sectional view of the handle portion shown in FIG. 9 with the optical fiber extending through the body tissue;

FIG. 13 is a perspective view of another alternate embodiment of the handle portion with the inner assembly in a fully extended position;

FIG. 14 is a perspective view of the handle portion shown in FIG. 13 with the inner assembly in a partially retracted position;

FIG. 15 is a perspective view with partial separation of parts of the handle portion shown in FIG. 13;

FIG. 16 is a partial cross-sectional view in perspective of the housing and spring biasing member of the handle portion shown in FIG. 15;

FIG. 17 is a perspective view with parts separated of the internal assembly of the handle portion shown in FIG. 13;

FIG. 18 is a partial side view in perspective of the housing and spring biasing member of the handle portion shown in FIG. 17;

FIG. 19 is a partial perspective view of the handle portion shown in FIG. 13 with a half-housing section removed;

FIG. 20 is a partial side cross-sectional view of the handle portion shown in FIG. 13;

FIG. 23 is a sectional view of the handle portion device shown in FIG. 13 adjacent body tissue with the inner assembly partially advanced and the optical fiber extending through body tissue;

FIG. 24 is a sectional view of the handle portion shown in FIG. 13 adjacent body tissue with the outer housing partially extended, the inner assembly partially advanced, and the optical fiber extending through body tissue;

FIG. 27 is a partial perspective view of the fiber control assembly of FIG. 26.

FIG. 29 is a cross sectional view of the optical fiber, fiber coating, fiber casing and upper retaining clip taken from FIG. 28.

FIG. 30 is a cross sectional view of the optical fiber, fiber coating and lower retaining clip taken from FIG. 28.

FIG. 31 is a partial view of the fiber control assembly and a side cross-sectional view of the handle portion shown in FIG. 2 engaging body tissue with the optical fiber retracted within the housing of the device; and FIG. 32 is a partial view of the fiber control assembly and a side cross-sectional view of the handle portion shown in FIG. 2 engaging body tissue with the optical fiber advanced into the body tissue.

DETAILED DESCRIPTION OF PREFERRED EMBODIMENTS

Figure 1:
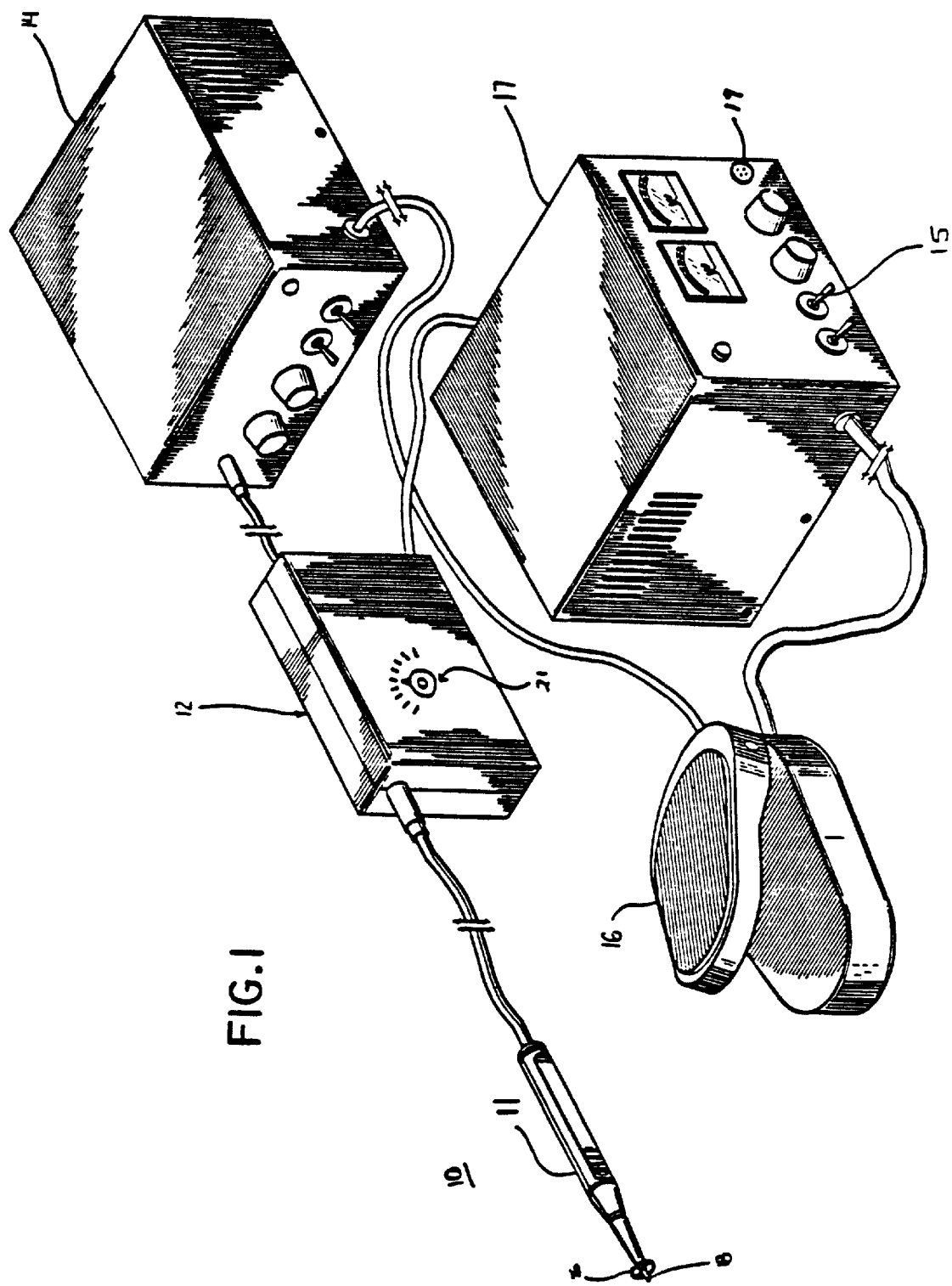
FIG. 1 is a perspective view of one embodiment of the laser ablation device in association with a control assembly.

Preferred embodiments of the laser ablation device will now be described in detail with reference to the drawings, in which like reference numerals designate identical or corresponding elements in each of the several views.

One embodiment of the presently disclosed laser ablation device will now be described with reference to FIGS. 1–8. FIG. 1 illustrates a laser ablation device shown generally at 10. Device 10 preferably includes handle portion 11, an optical fiber advancing mechanism 12, a laser generator 14, a foot operated actuator 16, and a control module 17. The optical fiber advancing mechanism 12 is of the type capable of precisely transmitting longitudinal motion and, optionally, rotational motion, to an optical fiber, optical fiber bundle or other laser energy transmission mechanism. The controlled longitudinal and/or rotational motion can be provided by one or more motors and preferably by one or more stepper motors. The stepper motors can be of the type commercially available from Haydon Switch and Instrument, Inc. of Waterbury, Connecticut or Eastern Air Devices, Inc. of Dover, New Hampshire. The laser generator 14 may be either a continuous wave laser or a pulsed, high energy laser; such as, for example, an excimer, $CO_2$, Yag, or an alexandrite laser. Preferably, a pulsed high energy xenon chloride excimer laser is used, such as those available from Spectranetics of Colorado Springs, Colo., or Medolas of Germany.

The optical fiber advancing mechanism 12 and the laser generator 14 are operably connected to foot switch 16. By depressing foot switch 16, laser energy is transmitted through the optical fiber by laser generator 14 while fiber advancing mechanism 12 advances the laser fiber relative to handle portion 11. As shown, the signal from foot switch 16 actuates control module 17 which communicates with fiber advancing mechanism 12. Control module 17 is programmable and controls the motors or similar advancing structure in advancing mechanism 12 upon actuation of foot switch 16. Control module 17 is shown with a receptacle 19 adapted to engage a terminal of a programmable computer to interface control module 17 with the computer. As such, instructions required to operate advancing mechanism 12 can then be stored in control module 17. Such instructions are commercially available, for example, through Intelligent Motions Systems, Inc. of Taftville, Connecticut. A toggle switch 15 may be provided on the control module 17 to switch from an operation mode to a test mode. In a particular test mode, when the foot actuator 16 is acted upon, the flexible optical fiber is moved sequentially from a retracted position, to a predetermined extended position, and back to the retracted position.

Fiber advancing mechanism 12 is preferably equipped with two internal limit switches (not shown). The first limit switch is preferably positioned to be activated when the optical fiber is at a desired retracted position (i.e., a "home" position), wherein the mechanism that is retracting the fiber is caused to stop. The second limit switch limits/controls the maximum distance that the optical fiber can extend from handle portion 11. Most preferably, an external selector 21 is provided so that the operator can select the desired maximum extension of the distal end of the optical fiber from the handpiece. For example, selector 21 can be in the form of a rotatable knob that can be set at selectable positions, wherein each position corresponds to a predetermined maximum longitudinal position of the optical fiber. When the fiber reaches the selected position, a limit switch can automatically terminate the fiber's advancement. In a most preferred embodiment, the operator can select fiber extension positions so that the distal end of the fiber extends from the distal end of the hand piece from between about 0.5 cm and about 5.0 cm, with the ability to select in increments of about 0.25 cm to about 0.5 cm. In the embodiment shown in FIGS. 26–32, the fiber preferably extends from the handpiece from between about 0.2 cm and about 4.0 cm, with the ability to select in increments of about 0.2 cm. The minimum and maximum extensions and the selected incremental values therebetween can be varied as desired.

Figure 2:
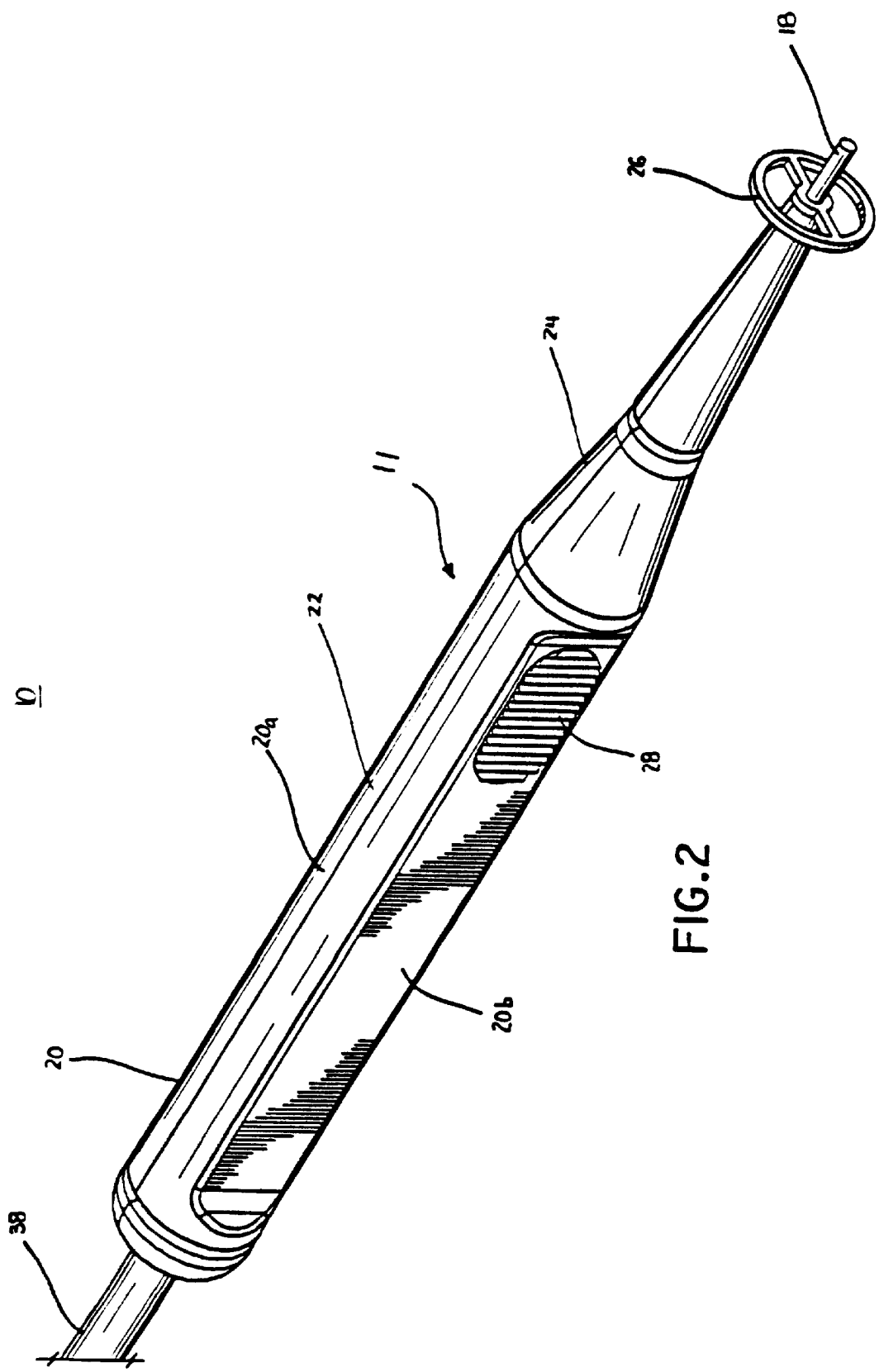
FIG. 2 is a perspective view of the handle and fiber optic portion of the laser ablation device shown in FIG. 1.

FIG. 2 illustrates a perspective view of the handle portion 11 of laser ablation device 10. Briefly stated, handle portion 11 includes housing 20 formed from molded housing half-sections 20a and 20b. Housing 20 has an elongated body 22 with a conically tapered section 24. An optional locator ring 26 is provided at the distal end of conically tapered section 24 that can be positioned in engagement with body tissue, i.e., the wall of the heart during a TMR procedure, to facilitate proper orientation of the handle portion with respect to the body tissue. Locator ring 26 can be formed integrally with housing half-sections 20a and 20b or can be removably fastened to tapered section 24. A ridged surface 28 is formed on an outer wall of housing half-sections 20a and 20b to facilitate grasping of the device 10.

FIG. 3 illustrates laser ablation device 10 with housing half-sections 20a and 20b and the internal components of the handle portion 11 separated. Housing half-sections 20a and 20b define a central bore 30, a proximal recess 32, and a distal recess 34. The proximal recess 32 is configured to receive a swivel connector 36 which is fastened to the optical fiber casing 38. The swivel connector 36 has an annular flange 40 dimensioned to be received within an increased diameter section 42 of proximal recess 32 to permit rotation of housing 20 with respect to optical fiber casing 38.

AS shown, the locator ring 26 has a cylindrical body portion 44 having an annular flange 46 formed at its proximal end. The cylindrical body portion 44 includes a central bore 50 and is configured to be received within the distal recess 34 defined by housing half-sections 20a and 20b. Central bore 50 of cylindrical body portion 44 is aligned with a central opening 48 formed in the distal end of the housing 20 and the central bore 30 of housing 20. Locator ring 26 can either swivel, to allow independent rotation of the handle portion relative thereto, or be fixed in place. The optical fiber 18 is slidably positioned within central bores 30 and 50 such that it can be advanced through opening 48 in housing 20. Pins or screws 49 can be used to fasten the housing half-sections 20a and 20b together to secure the locator ring 26 and the swivel connector 36 to the housing 20.

FIGS. 4–5A illustrate laser ablation device 10 during use in a TMR procedure. Locator ring 26 has been positioned against the epicardium 54 of the heart 56. Because the heart may be beating during a TMR procedure, the locator ring 26 greatly enhances the surgeon's ability to position and stabilize the laser ablation device 10 with respect to the heart 56. In FIG. 4, the foot operated actuator 16 (FIG. 1) has not been actuated and the optical fiber 18 is in a retracted position with its distal end 60 positioned in central bore 50 of locator ring 26.

Referring now to FIGS. 5 and 5A, foot operated actuator 16 (FIG. 1) has been actuated to initiate operation of laser generator 14 and the advancing mechanism 12 to ablate tissue and advance optical fiber 18. The distal end 60 of optical fiber 18 has been advanced in the direction indicated by arrow "A" to produce a channel 57 from the epicardium through to the myocardium 58 in the ventricle of the heart 56. During the TMR procedure, 1 or more channels can be ablated into the heart to facilitate blood delivery to ischemic areas of the heart. The distal end 60 of the optical fiber 18 which can be a single fiber or a bundle or fibers, is preferably advanced at a rate that is coordinated with the power level and the frequency of pulsing of the laser generator to form channels in the heart. For example, optical fiber 18 can be advanced at a rate of between about 0.5 mm/sec (0.02 in/sec) to about 12.7 mm/sec (0.5 in/sec) with a laser power level of about 10 mJ/mm$^2$ to about 60 mJ/mm$^2$ and a pulsing frequency of about 5 Hz to about 100 Hz. Preferably, the optical fiber is advanced at a rate of about 1.0 mm/sec to about 2.0 mm/sec with a laser power level of between about 30 mj/mm$^2$ to about 40 mJ/mm$^2$ and a pulse frequency of about 50 Hz. In a most preferred embodiment, the rate of advancement of the optical fiber is no greater than the rate of ablation of tissue in order to minimize mechanical tearing by the fiber. Alternatively, if some degree of mechanical tearing is desired, the advancing mechanism can be set to advance the fiber at a rate greater than the ablation rate. Studies have shown that a xenon chloride excimer laser operating at a power level of about 35mJ/mm$^2$ can ablate about 30–35 microns of animal heart tissue per pulse.

In one study, channels were successfully created in canine heart tissue using a xenon chloride excimer laser (308 nm) optically connected to a 1.8 mm solid fiber bundle. The laser was set to provide about 30 mJ/mm$^2$ at a rate of about 50 Hz, while the advancing mechanism was set to advance the laser fiber bundle at various constant speeds between about 1.3 mm/sec (0.05 in/sec) and about 13 mm/sec (0.5 in/sec). In a clinical trial on a human heart, the laser was set to provide about 35 mJ/mm$^2$ at a rate of about 30 Hz with a feed rate of about 0.95 mm/sec (i.e., advancing the fiber at approximately 1.25 thousandths if an inch per pulse).

Typically, a healthy heart has a wall thickness of 10–15 mm. A diseased heart may be as thick as 40 mm (measured from the outer surface of the epicardium to the inner wall of the myocardium). At a minimum, the laser ablation device 10 and control assembly should be capable of advancing the optical fiber 18 through a stroke having a length at least as great as the thickness of the heart being treated. Alternately, it is possible to create channels in the myocardium from within the heart by introducing the laser fiber into the patient's vasculature or through an opposing heart wall and directing the fiber tip to the desired location. See, for example, U.S. Pat. No. 5,389,096 to Aita et al. In this approach, once the fiber is properly placed, controlled advancement of the fiber can be achieved as described above. However, with this approach the fiber preferably will not penetrate the epicardium.

Referring now to FIGS. 6–8, laser fiber 18 and fiber advancing mechanism 12 (FIG. 1) can also be used to perform laser angioplasty. During the laser angioplasty procedure, the optical fiber 18 is inserted into a blood vessel 62 such that the distal end 60 of the optical fiber 18 is positioned adjacent a plaque obstruction 64 (FIG. 6), as is known in the art. The foot operated actuator 16 (FIG. 1) is actuated to initiate operation of the advancing mechanism 12 and the laser generator 14 to simultaneously advance, in the direction indicated by arrow "B", and ablate plaque 64 to produce a channel 66 through the obstruction. As discussed above, the rate of advancement of the optical fiber 18 and the power level and frequency of pulsing of laser energy are coordinated, via control module 17, to form the channel 66 through the plaque. By precisely controlling the rate of advancement of the laser fiber, the user can ensure that the plaque is truly ablated by the laser energy and not just pushed aside. Ablation/removal of plaque reduces the likelihood of or delays restenosis as compared to mere mechanical manipulation of the plaque.

An alternate, preferred embodiment of the presently disclosed laser ablation device will now be described with reference to FIGS. 9 to 12. The handle portion of the laser ablation device shown in this embodiment has a self-biasing advancing mechanism incorporated therein. FIGS. 9 and 10 illustrate the handle portion of the laser ablation device shown generally as 100. Briefly described, handle portion 100 includes a housing 120 formed from molded housing half-sections 120a and 120b. The housing half-sections 120a and 120b are formed with mating recesses 114 configured to slidably receive the internal components. A proximal opening 115 and a distal opening 116 are formed in housing 120 to permit an optical fiber 118 to extend through the housing 120. A swivel connector (such as 36 in FIGS. 3–5A) and fiber casing (such as 38 in FIG. 3) can also be included.

An engagement assembly 113 is slidably positioned within a channel 122 defined by mating recesses 114 formed in housing half-sections 120a and 120b. The engagement assembly 113 includes a cylindrical cap 124, a flexible engagement washer 128, and a compression screw 130. The cylindrical cap 124 has a threaded blind bore 126 dimensioned to receive the flexible engagement washer 128. The compression screw 130 has a threaded end 134 dimensioned to be threaded into the blind bore 126. The cylindrical cap 124, the engagement washer 128 and the compression screw 130 all have a central throughbore to permit the optical fiber 118 to extend through the housing 120.

Referring to FIG. 10A, the engagement washer 128 is positioned in the blind bore 126 of cylindrical cap 124 and compression screw 130 is threaded into the blind bore 126. As the engagement washer 128 is compressed between the compression screw 130 and the base of blind bore 126, the washer 128 deforms inwardly into frictional engagement with the optical fiber 118 to fasten the optical fiber 118 to the engagement assembly 113.

The advancing assembly 112 includes a guide member 136 and a biasing member 138. The guide member 136 is positioned in abutting relation with the proximal end of the cap 124 of engagement assembly 113. An elongated rib 140 extends along the longitudinal periphery of guide member 136 and is configured to be received within a longitudinal slot 142 formed on an internal wall of the housing 120. The rib and slot engagement limits rotation of the guide member 136 with respect to the housing 120 to avoid inadvertent disengagement of the guide member 136 and biasing member 138.

The biasing member 138 is positioned to engage the proximal end of the guide member 136 as to bias the guide member 136 distally into the engagement assembly 113 to move the engagement assembly 113 distally in channel 122. The biasing member 138 preferably includes a constant force spring having a first end 144 connected through an opening 146 to the housing 120 and a body portion 148 positioned in a recess 150 formed in the proximal end of the guide member 136. The constant force spring allows for controlled advancement of the laser fiber, which has advantages in TMR and angioplasty procedures, similar to those previously described.

Figure 11:
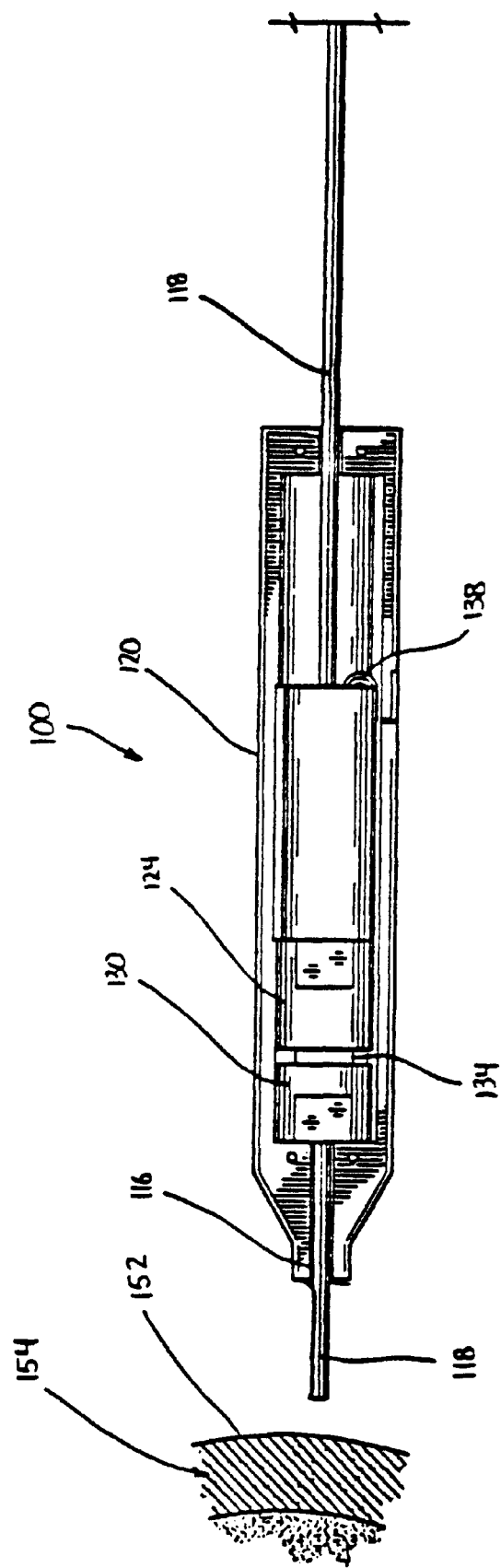
FIG. 11 is a side cross-sectional view of the handle portion shown in FIG. 9 positioned adjacent to body tissue with the optical fiber extended.

FIGS. 11–12 illustrate the handle portion 100 of laser ablation device during use in a TMR procedure. FIG. 11 illustrates the handle portion 100 prior to engagement with heart 152. The biasing member 138 has moved the guide member 136 into abutment with the engagement assembly 113 to advance the engagement assembly distally in channel 122. Because of the frictional connection between washer 128 and optical fiber 118, optical fiber 118 has been advanced distally with the engagement assembly 113 and extends through opening 116 in housing 120.

Referring now to FIG. 11A, the handle portion 100 of laser ablation device has been pushed against the epicardium 154 of the heart 152. The force on the distal end of the optical fiber 118 is sufficient to overcome the force of the biasing member 138 to retract the optical fiber 118, in the direction indicated by arrow "C", to a position within housing 120. It is noted that the strength of the biasing member should be less than that capable of puncturing the heart 152, e.g., the optical fiber 118 should not pierce the heart when the distal end of the optical fiber is pushed against the epicardium.

In FIG. 12, laser energy has been conducted to the optical fiber 118 to ablate heart tissue adjacent the distal end 160 of the optical fiber 118. As the heart tissue adjacent the distal end 160 of the optical fiber is ablated, biasing member 138 continually advances the optical fiber 118, in the direction indicated by arrow D through the heart tissue until a channel 162 is formed in the ventricle of the heart from the epicardium through the myocardium 156. The laser energy level and pulse frequency are coordinated with the rate of advancement provided by the biasing member 138. A similar biasing mechanism can be used to controllably advance the laser fiber during laser angioplasty.

A further alternate, preferred embodiment of the presently disclosed laser ablation device is shown in FIGS. 13–25. The handle portion 200 of the laser ablation device in this embodiment includes a self-biasing advancing mechanism substantially identical to that incorporated in the handle portion 100 described above. The device further includes a compensating mechanism suitable for use in performing a TMR procedure on a beating heart.

FIGS. 13 and 14 illustrate the handle portion of laser ablation device shown generally as 200. Briefly, handle portion 200 includes an outer housing 210 formed from molded housing half-sections 210a and 210b and an inner housing 220 formed from molded housing half-sections 220a and 220b. The inner housing 220 is slidably positioned within outer housing 210, as indicated by arrow "E", and includes a distal conical portion 222 having an opening 224 dimensioned to permit passage of an optical fiber 218.

Referring now to FIGS. 15 and 16, the outer housing half-sections 210a and 210b have recesses which together form a channel 226 in which the inner housing 220 is slidably positioned. Proximal and distal openings 228 and 230 are also formed in the outer housing 210 and are dimensioned to permit passage of the optical fiber 218 and the inner housing 220, respectively. As with the previous embodiment, a swivel connector (such as 36 in FIGS. 3–5A) and fiber casing (such as 38 in FIG. 3) can also be included but are not shown. A biasing member 232 is positioned within the outer housing 210 to engage and urge the inner housing 220 towards the distal end of channel 226. The biasing member 232 can be a spring having a first portion retained in a slot 234 formed in the outer housing 220 and a second portion engaging a retainer 236 secured to the inner housing 220. The outer housing half-sections 220a and 220b can be fastened together with pins or screws 238 to secure inner housing 220 within channel 226.

FIGS. 17–20 illustrate the inner housing 220 with parts separated. The internal components of the inner housing 220 include an engagement assembly and an advancing mechanism, which are similar to those disclosed with respect to the housing portion 100 and will only be briefly discussed herein. The engagement assembly includes a cylindrical cap 240, a flexible engagement washer 242, and a compression screw 244. The cylindrical cap 240 has a threaded blind bore 245 which is adapted to receive a threaded end 246 of compression screw 244. The compression screw 244 is threaded into blind bore 245 to compress and deform the engagement washer 242 into frictional engagement with optical fiber 218, which extends through a central bore formed in the engagement assembly.

The advancing mechanism includes a guide member 248 and a biasing member 250. The guide member 248 is positioned in abutting relation to the proximal end of cap 240. The biasing member 250 is positioned to engage and bias the guide member 248 distally within a channel 252 formed in the inner housing 220 to move the engagement assembly towards the distal end of the channel 252. An elongated rib 254 is formed on the outer periphery of the guide member 248 and is received in a slot 256 formed along channel 252 to prevent the guide member 248 from rotating and becoming disengaged from the biasing member 250. The inner housing half-sections can be fastened together with pins 258 to secure the engagement assembly and the advancing mechanism within channel 252.

Figure 21:
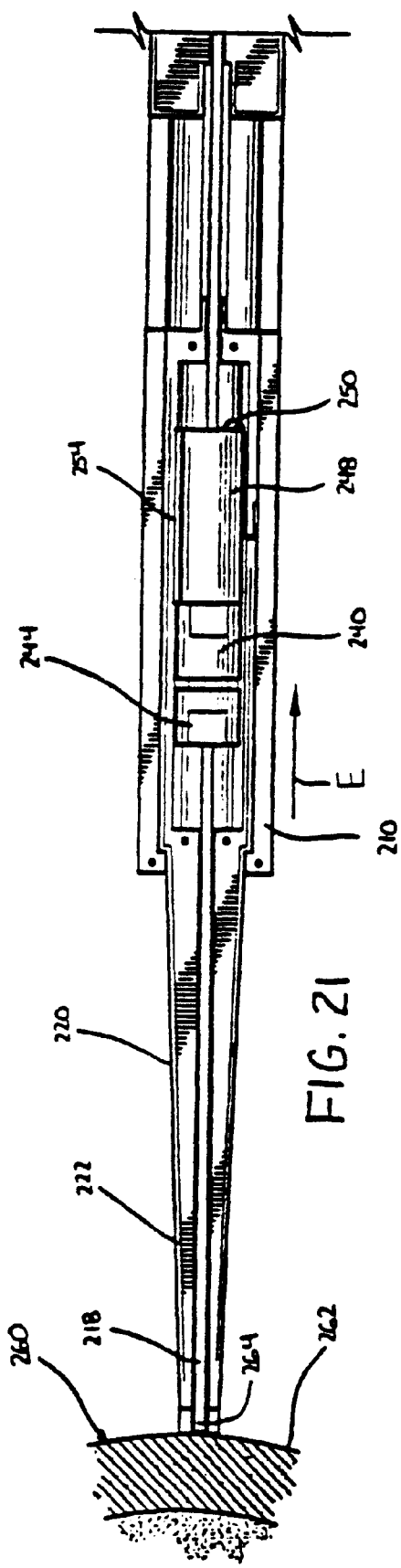
FIG. 21 is a sectional view of the handle portion shown in FIG. 13 adjacent body tissue.

FIGS. 21–25 illustrate a handle portion 200 of a laser ablation device during use in a TMR procedure. FIG. 21 illustrates the handle portion 200 after the optical fiber 218 has been pressed against the epicardium 262 of the heart 260 but before laser energy has been conducted to the optical fiber 218. Engagement between the distal end 264 of optical fiber 218 creates a compressive force in the optical fiber 218 that overcomes the force of biasing member 250 to cause retraction of the optical fiber 218 in the direction indicated by arrow "E".

Figure 22:
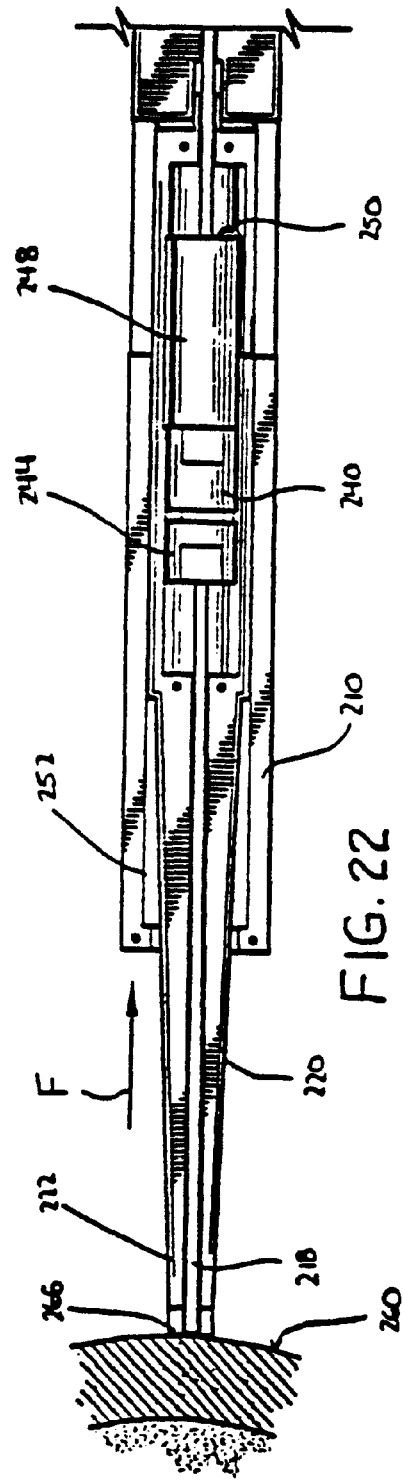
FIG. 22 is a sectional view of the handle portion shown in FIG. 13 adjacent body tissue with the inner assembly and optical fiber retracted.

Referring to FIG. 22, the distal end 266 of the inner housing 220 is positioned in abutting relation with the heart 260. If the heart 260 and the handle portion 200 move towards each other with the handle portion 200 in this position, such as when the heart beats or the patient breathes, the force on the distal end 264 of inner housing 220 overcomes the force of biasing member 232 (FIG. 19), to permit the inner housing 220 to move proximally within channel 252, in the direction indicated by arrow "F". Outer housing 210 and biasing member 232 form a compensation assembly in this respect.

Figure 25:
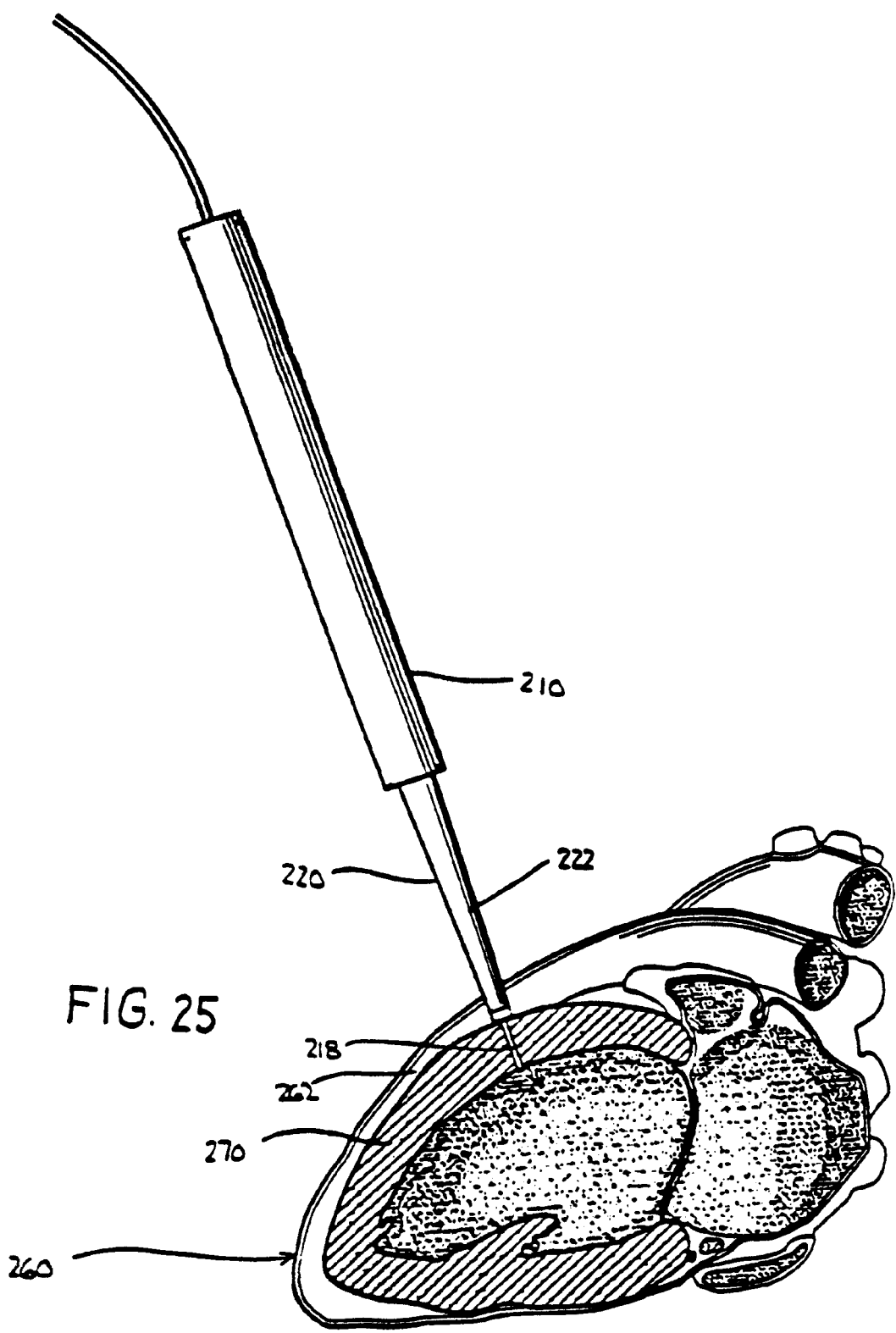
FIG. 25 is a side partial cross-sectional view of the handle portion shown in FIG. 13 and a heart during a TMR procedure with the optical fiber extending through the myocardium.

Referring now to FIGS. 23–25, laser energy has been conducted to the optical fiber 218 to ablate heart tissue adjacent to the distal end 264 of the optical fiber 218. As the heart tissue is ablated, biasing member 250 controllably advances distal end 264 of optical fiber 218, in the direction indicated by arrow "G", through the heart tissue until a channel 268 is formed from the epicardium 262 through the myocardium 270. Once again, the power output of the laser generator conducting energy to optical fiber 218 is coordinated with the advancement mechanism to provide channels 268 in the heart.

Referring now to FIGS. 26–32, an alternate laser ablation device is shown, wherein the control module (generally shown as 17 in FIG. 1) and fiber advancing assembly (generally shown as 12 in FIG. 1) have been combined into a single unit refereed herein as fiber control assembly 312. Fiber control assembly 312 is shown on top of laser energy generator 314 and is positioned to receive an optical fiber that serves to transmit laser energy from laser 314 to body tissue. Laser 314 is preferably an excimer laser, however, other laser energy sources that can be coupled to an optical fiber can also be used. Laser 314 is also shown with a control pad 316 and a monitor 318. Footswitch 320 is also shown and serves to actuate the laser and fiber control assembly.

With reference to FIGS. 27–30, fiber control assembly 312 is shown in greater detail. Fiber control assembly houses motor 322 (preferably a stepper motor) that serves to move lower fiber securing plate 324 relative to upper fiber securing plate 326. Upon actuation, motor 322 rotates screw 328 relative to threads disposed in lower plate 324 (not shown) to move the lower plate relative to the upper plate. Both the upper plate and the lower plate have clip recesses 341 and 343, respectively, and clips 342 and 344, respectively, that serve to hold portions a disposable lasing assembly, discussed in greater detail below. The motor and plates are disposed in housing portion 330 that includes movable access door 332 and upper fiber exit opening 334 and lower fiber entrance opening 336. Fiber control assembly also includes rotatable depth selector 338 that allows the user to select the desired movement of lower plate 324 relative to upper plate 326. As discussed in greater detail, below, movement of the lower plate relative to the upper plate controls movement of the optical fiber relative to a handle portion. Preferably, the selected depth is displayed on digital display panel 340 and is selectable in 0.2 cm increments in a range between about 0.2 cm to about 4.0 cm.

Figure 28:
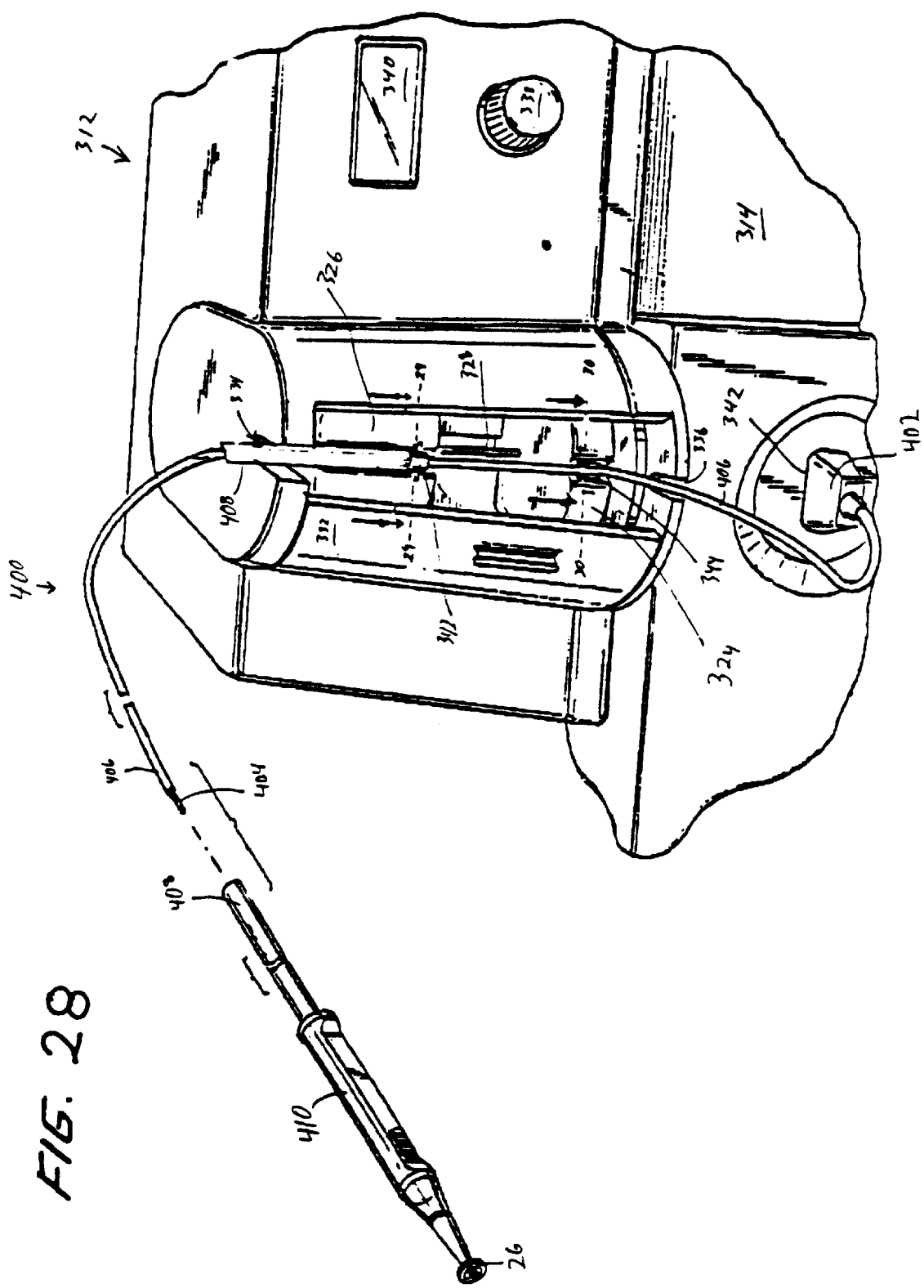
FIG. 28 is a partial perspective view of the fiber control assembly of FIG. 27 with the optical fiber and fiber casing mounted to the fiber control assembly.

Turning to FIGS. 28–30, a disposable lasing assembly, generally designated as 400, is shown connected to fiber control assembly 312 and laser energy generator 314. Disposable lasing assembly 400 includes coupler 402, optical fiber 404, fiber casing 408 and handle portion 410. Coupler 402 is configured and dimensioned to be connected to laser generator 314 at laser output 342, wherein energy emitted from the laser is directed into the proximal end of optical fiber 404. Optical fiber 404 is shown as a bundle of fibers but can also be a single fiber. Optical fiber 404 preferably has fiber coating 406 (see FIGS. 29 and 30) that is preferably at least partially stripped away from the distal of the fiber (see FIGS. 31 and 32) so that only the fiber touches body tissue. Fiber casing 408 serves to provide a fixed distance between handle portion 410 and upper plate 326. The casing can be ratably connected to either or both the handle portion (as described above) and the upper plate. Optical fiber 404 is movable within casing 408. Handle portion 410 is similar handle portion 11, described above.

To connect disposable lasing assembly 400 to the laser and fiber control assembly, the surgeon or operator will attach coupler 402 to laser output 342, pass optical fiber 404 (and coating 406 disposed about the fiber, if included) through lower fiber entrance opening 336, secure the fiber to lower plate 324 by means of clip 344, secure fiber casing 408 to upper plate 326 by means of clip 342 and direct the fiber casing and fiber out of the control assembly through upper fiber exit opening 334. These steps of connecting the disposable lasing assembly to the control assembly need not be performed in any particular order. Because the disposable lasing assembly passes through openings 336 and 334, door 322 can be closed during operation.

Figure 26:
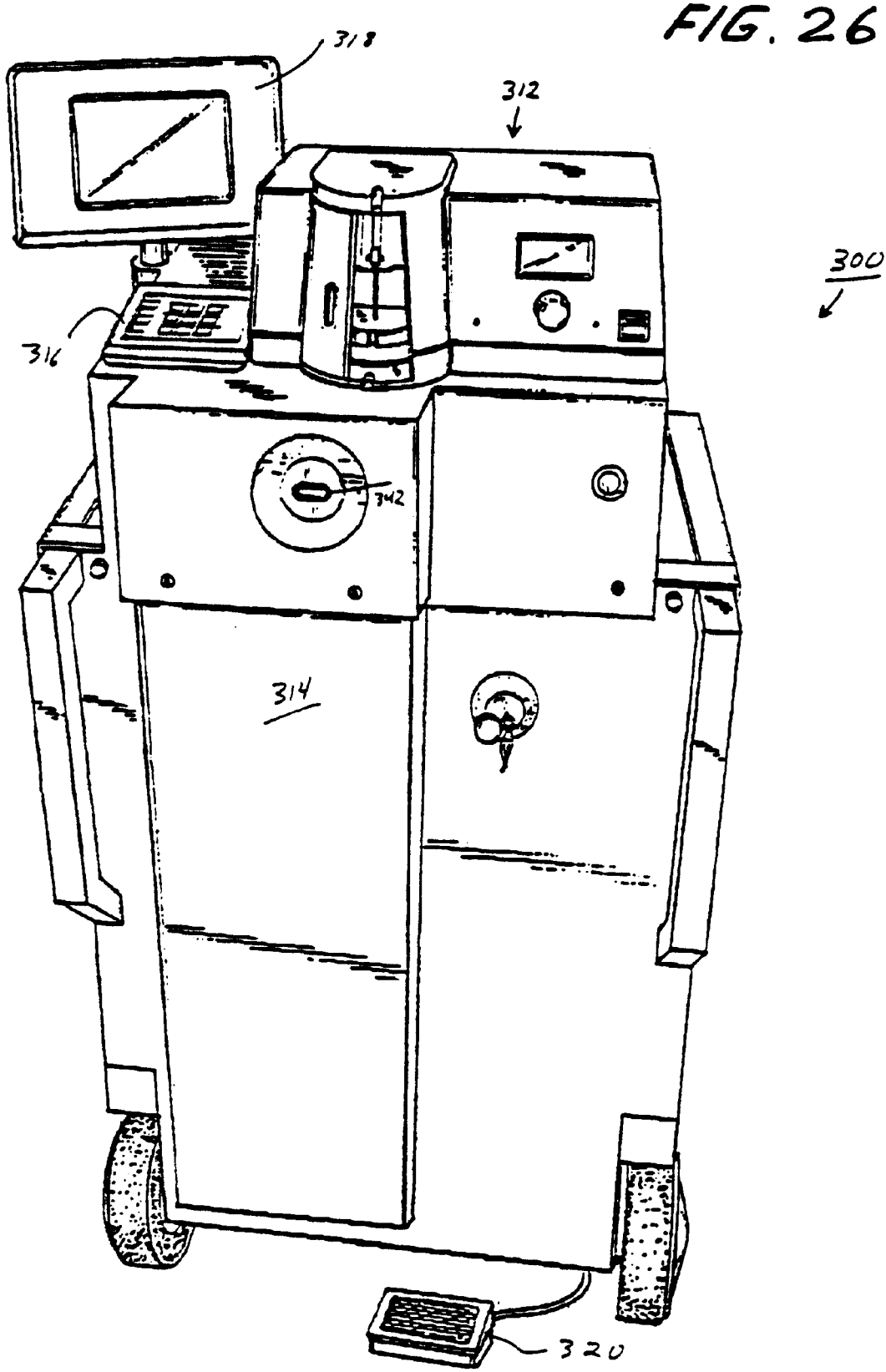
FIG. 26 is a perspective view of an alternate embodiment of a laser ablation device wherein the control module and fiber advancing assembly have been combined into a single unit.

During operation, with reference to FIGS. 31 and 32, the surgeon or operator will use depth selector 338 to select the desired depth that the distal end of optical fiber 404 will feed into the body tissue 500. Next the surgeon places the distal end of handle portion 410 at a desired location against the tissue (i.e., heart tissue) and activates foot switch 320 (FIG. 26). The foot switch activates motor 322 and laser generator 314. Motor 322 rotates screw 328 to move lower plate 324 towards upper plate 326 in the direction of arrow A. Because fiber casing 408 is secured at both ends (one end to handle portion 410 and the other to upper plate 326) and the optical fiber is secured to the lower plate, movement of the lower plate a distance X causes the distal end of the optical fiber to move a distance X relative to the distal end the handle portion. Once the desired distance X has been traveled, laser energy transmission is stopped and motor 322 reverses direction to bring the optical fiber to its initial or "home" position. The procedure can be repeated according to the discretion of the surgeon.

After the surgeon has finished with a particular patient, disposable lasing assembly 400 can be discarded and laser generator 314 and fiber control assembly 312 can be cleaned for the next patient. Disposable lasing assembly 400, in combination with the relatively quick and easy to use connection to the laser generator and fiber control assembly, provides for a convenient and safe method of performing laser surgery, such as TMR.

It will be understood that various modifications can be made to the embodiments disclosed herein. For example, in the first embodiment, any type of motor, such as air, hydraulic, pneumatic or other electrical motor can be used in place of a stepper motor. In addition, alternate devices can be used to actuate the laser advancing device and the laser energy source, such as a trigger mechanism associated with the handle portion. Also, various other structures for securing the optical fiber and fiber casing to the fiber control assembly can be used. Therefore, the above description should not be construed as limiting, but merely as exemplifications of preferred embodiments. Those skilled in the art will envision other modifications within the scope and spirit of the claims appended thereto.

What is claimed is:

1. A laser ablation device comprising:

a handle portion having proximal and distal openings;

a fiber advancing device having a stationary member and a movable member, the movable member being movable towards and away from the stationary member;

a fiber casing having proximal and distal ends, the distal end being secured to a proximal end of the handle portion and the proximal end being secured to the stationary member of the fiber advancing device;

at least one optical fiber having proximal and distal ends, the distal end being extendible through the handle portion and a portion of the fiber defined between the proximal and distal ends being secured to the movable member of the fiber advancing device; and a laser energy generator optically connected to proximal end of the at least one optical fiber;

said handle portion including a self-biasing advancing mechanism comprising:

a guide member positioned within at least a portion of a channel extending within said handle portion; and at least one biasing member operatively connected to the guide member to guide the guide member proximally as a proximal force is applied to the distal end of said at least one optical fiber and to guide the guide member distally when laser energy is transmitted to the at least one optical fiber by the laser energy generator.

2. The laser ablation device according to claim 1, wherein said at least one biasing member includes a spring.

3. The laser ablation device according to claim 2, wherein the spring is a constant force spring.

4. The laser ablation device according to claim 1, wherein said handle portion further comprises a second biasing member at a proximal end of an inner housing disposed within said handle portion, the second biasing member permitting relative movement between the handle portion and the inner housing.

5. The laser ablation device according to claim 1, wherein the laser energy generator is designed to pulse at a predetermined frequency and at a predetermined energy level and the fiber advancing device simultaneously advances the at least one optical fiber at a predetermined, constant rate to ablate body tissue.

6. The laser ablation device according to claim 1, further comprising a compensation assembly operably connected to the handle portion.

7. The laser ablation device according to claim 1, wherein the guide member includes an elongated rib on an outer periphery which is received in a slot formed along said channel to prevent the guide member from rotating and becoming disengaged from the at least one biasing member.

* * * * *